(12) United States Patent
Shirai et al.

(10) Patent No.: US 10,646,869 B2
(45) Date of Patent: May 12, 2020

(54) FLOW CELL DEVICE FOR SINGLE CELL ANALYSIS, AND SINGLE CELL ANALYSIS DEVICE

(71) Applicant: HITACHI, LTD., Tokyo (JP)

(72) Inventors: Masataka Shirai, Tokyo (JP); Tomoyuki Sakai, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 320 days.

(21) Appl. No.: 15/544,888

(22) PCT Filed: Feb. 3, 2015

(86) PCT No.: PCT/JP2015/052965
§ 371 (c)(1),
(2) Date: Jul. 20, 2017

(87) PCT Pub. No.: WO2016/125251
PCT Pub. Date: Aug. 11, 2016

(65) Prior Publication Data
US 2018/0304262 A1    Oct. 25, 2018

(51) Int. Cl.
*B01L 3/00* (2006.01)
*B01L 1/00* (2006.01)
(Continued)

(52) U.S. Cl.
CPC ... *B01L 3/502761* (2013.01); *B01L 3/502715* (2013.01); *C12M 1/00* (2013.01);
(Continued)

(58) Field of Classification Search
CPC .......... B01L 3/50273; B01L 3/502761; C12M 35/00; C12M 35/04
See application file for complete search history.

(56) References Cited

U.S. PATENT DOCUMENTS 5,674,743 A * 10/1997 Ulmer .................. B01J 19/0046
                                                                435/287.2
2009/0098541 A1* 4/2009 Southern ........... B01L 3/502753
                                                                435/6.11
(Continued)

FOREIGN PATENT DOCUMENTS

| JP | 2010-051291 A | 3/2010 |
| JP | 2013-058138 A | 3/2013 |
| WO | 2014/020657 A1 | 2/2014 |

OTHER PUBLICATIONS

Saiful Islam, et al., "Characterization of the single-cell transcriptional landscape by highly multiplex RNA-seq", Genome Research, vol. 21, No. 7, 2011, pp. 1088.
(Continued)

*Primary Examiner* — Nathan A Bowers
(74) *Attorney, Agent, or Firm* — Mattingly & Malur, PC

(57) ABSTRACT

(1) Plural reaction chambers each including at least one cell capturing unit and at least one nucleic acid capturing unit connected via a flow channel, (2) a first liquid flow channel commonly connected to the plural reaction chambers on a first surface side, (3) plural second liquid flow channels connected to the plural reaction chambers in a one-on-one relationship on the first surface side, and (4) a third liquid flow channel commonly connected to the plural reaction chambers on a second surface side opposite to the first surface, are provided in a flow cell device for single cell analysis.

15 Claims, 16 Drawing Sheets

(51) Int. Cl.
*G16B 30/00* (2019.01)
*C12M 1/00* (2006.01)
*C12N 15/10* (2006.01)
*C12Q 1/6869* (2018.01)
*C12Q 1/6876* (2018.01)

(52) U.S. Cl.
CPC ..... *C12N 15/1003* (2013.01); *C12N 15/1096* (2013.01); *C12Q 1/6869* (2013.01); *C12Q 1/6876* (2013.01); *G16B 30/00* (2019.02); *B01L 2200/0668* (2013.01); *B01L 2300/161* (2013.01); *B01L 2400/049* (2013.01); *B01L 2400/0688* (2013.01)

(56) References Cited

U.S. PATENT DOCUMENTS

| | | | |
|---|---|---|---|
| 2012/0071358 A1* | 3/2012 | Zhou | B01L 3/502746 506/26 |
| 2012/0245053 A1* | 9/2012 | Shirai | C12N 15/1093 506/9 |
| 2013/0067418 A1 | 3/2013 | Fukazawa | |
| 2015/0167063 A1 | 6/2015 | Shirai et al. | |
| 2017/0113224 A1* | 4/2017 | Feiglin | B01L 3/0268 |

OTHER PUBLICATIONS

International Search Report of PCT/JP2015/052965 dated Apr. 21, 2015.

\* cited by examiner

FLOW CELL DEVICE FOR SINGLE CELL ANALYSIS, AND SINGLE CELL ANALYSIS DEVICE

TECHNICAL FIELD

The present invention relates to a flow cell device for single cell analysis and a single cell analysis apparatus including the same.

BACKGROUND ART

Single cell analysis is a technique for detecting biological molecules in cells on a single cell basis with a high degree of precision and quantifying the molecules. Single cell analysis is roughly composed of two techniques. One is a technique of isolating a cell for analysis, and another is a technique of a sample preparation for measurement in a highly efficient manner from a tiny amount of the biological molecules in one cell and analyzing the sample.

In the former technique, a flow cytometer is generally used. In a flow cytometer, complicated processing is automated, and a user can isolate a cell easily. Meanwhile, a flow cytometer remains expensive. Recently, as a method for isolating a cell more easily and inexpensively, methods using a flow cell device have been known (PTLs 1 and 2).

PTL 1 discloses a configuration in which, for the purpose of isolating a cell of a kind to be measured, plural cell capturing units for individually capturing a cell into a reaction chamber in a flow cell device are disposed in an array form. The cell capturing unit is a device including a membrane filter which can isolate cells introduced into the reaction chamber in the flow cell device one by one. The target cells can not pass through apertures formed in the filter and are captured on the filter and isolated, whereas cells other than the target cells pass through the apertures in the filter and are discharged from the opposite side of the filter. The captured cells are measured by using a fluorescent label introduced by an immunostaining method for staining a membrane protein expressed on a cell membrane, or other methods.

PTL 2 discloses a device and an apparatus for capturing one cell from multiple cells (isolating a cell from multiple cells) and collecting the captured cell. In the case of PTL 2, the cell is captured by suction to a small hole, and thereafter only the target cell is sucked into a reaction chamber by controlling a valve, while discharging other cells than the target cell from the cell capturing unit.

Next, a technique used in a gene expression analysis at a single cell level will be described.

In a previous gene expression analysis realized by a single cell analysis, a method including taking an mRNA from a group of cells, then producing a cDNA which is a complementary strand and subjecting the cDNA to PCR amplification, and further capturing the target to a corresponding probe position using a DNA prove array (DNA chip) to perform fluorescent detection has been used.

However, methods using PCR amplification and a DNA chip have a low precision as a quantification analysis, and a more highly precise method for analyzing a gene expression profile has been demanded. In addition, with the completion of the human genomic analysis, demand for quantitatively investigating gene expressions is increasing, and meanwhile, heterogeneity on a single cell basis in a tissue is attracting attentions. A method for extracting mRNAs from a large number of single cells and quantitatively analyzing the mRNAs is thus demanded.

Recently, a method including subjecting a tiny amount of mRNAs in a single cell to reverse transcription to convert the mRNAs to cDNAs, subjecting the cDNAs to PCR amplification, determining the sequences of the amplification products using a large scale DNA sequencer, and calculating the sequencing results to count the number of the nucleic acid sequences after amplification, thereby estimating the number of the mRNA molecules is beginning to be used (NPL 1). In this method, since the upper limit of the number of measurable genes depends on the number of the parallel provisions of the large scale sequencer, all genes of 20 and several thousand can be measured, and in principle, 100 thousand kinds of sequences including the splicing variant can be measured.

In PTL 3, in order to realize a gene expression analysis of each individual cell at the same time for a large number of cells, a device is disclosed in which a $1^{st}$ cDNA library is formed using a porous membrane or a membrane device having a large number of beads packed therein, and further a two dimensional distribution of the gene expression is obtained from the library, thereby realizing a gene expression analysis in a large number of cells. In the analysis of gene expression in a single cell using the device, complementary strands ($2^{nd}$ cDNAs) are synthesized from the $1^{st}$ cDNAs built on the device and subjected to PCR amplification to prepare a sample (sequencing library) for a large scale sequence analyzer.

Since the sequencing library is prepared not for each cell but for each device, there becomes a state where nucleic acids from multiple cells are mixed. In PTL 3, in order to identify a cell on the device from the obtained sequence analysis data, a sequence unique for each position on the device is introduced in the $1^{st}$ cDNA library, and the results of the sequence analysis obtained by the large scale sequence analyzer are classified for each sequence unique for the position, thereby realizing a gene expression analysis at the single cell level.

CITATION LIST

Patent Literature

PTL 1: JP-A-2013-58138
PTL 2: JP-A-2010-51291
PTL 3: WO2014/020657

Non Patent Literature

NPL 1: Genome Research, Vol. 21, No. 7, 2011, p. 1088 (Genome Research, Vol. 21, No. 7, (2011) p. 1088)

SUMMARY OF INVENTION

Technical Problem

In practical research of regenerative medicine, research of diagnosis of cancers and immunity-related diseases by gene analyses, or basic study of biological phenomena of multicellular organisms, great attention is beginning to be focused on analyzing not only the expression levels of genes as an average of the tissue but also the components of the cells constituting the tissue one by one in a quantitative manner. That is, it is demanded to quantitatively monitor the expression levels of various genes by taking cells one by one. When gene mRNAs that act in a biological tissue can be measured at one cell level, various phenomena occurring in an organism can be understood in detail including interaction among cells, which is expected to provide great effects on research and diagnosis in the life science field, in particular, in the medical or drug design field.

On the other hand, when an essential process for placing cells each isolated using a flow cytometer one by one into a reaction tube to build up a sequencing library for the gene expression analysis (mRNA extraction, $1^{st}$ cDNA synthesis, $2^{nd}$ cDNA synthesis, nucleic acid amplification) is conducted entirely by a manual operation, several microliters or more of reagents are required, and in addition, the cost of the reagents increases in proportion to the cell number, resulting in a high reagent cost. In addition, the aforementioned manual operation is required to be performed by a veteran engineer.

In fact, also in the method described in PTL 1 or PTL 2, although it is possible to perform the isolation of a cell and the identification and measurement of the cell by a fluorescent label, the regulation of a sequencing library on each cell for a detailed gene expression analysis has to be conducted by transferring the isolated cells individually into a commercially-available plastic tube (or a 96-well plate or a 384-well plate) by a manual operation, and then separately implementing reactions from the mRNA extraction to the PCR amplification. In this case, the lower limit of the amount of a reagent required depends on the controllable volume in the manual operation (generally approximately 1 µL). For this reason, the amount of the reagent required increases in proportion to the cell number, unfortunately resulting in increase in the reagent cost for analysis.

As described above, any of the patent literatures do not assume that all the steps of the single cell analysis are performed in a single flow cell device. Incidentally, in the implementation of the analysis, it is required to perform a uniform sample preparation in an identical condition for a uniform cell group captured in a cell capturing units in the flow cell device to enable detailed gene expression for each single cell, and to realize individual treatments simultaneously for plural different cells. Here, for achieving a uniform sample preparation, it is required to supply a reaction solution from an identical reaction vessel, and for achieving a simultaneous implementation of the individual treatments, an individual reagent condition for each cell group is required to be applied. However, a technique for realizing the above two requirements without complicating the configuration of the flow cell device is currently not known.

Solution to Problem

One aspect of the flow cell device for single cell analysis of the present invention for solving the above problem is a flow cell device for single cell analysis, including (1) plural reaction chambers each including at least one cell capturing unit and at least one nucleic acid capturing unit connected via a flow channel, (2) a first liquid flow channel that is commonly connected to the plural reaction chambers on a first surface side, (3) plural second liquid flow channels that are connected to the plural reaction chambers in a one-on-one relationship on the first surface side, and (4) a third liquid flow channel that is commonly connected to the plural reaction chambers on a second surface side opposite to the first surface.

Furthermore, another aspect of the flow cell device for single cell analysis of the present invention for solving the above problem is a flow cell device for single cell analysis, including (1) plural reaction chambers each including at least one cell capturing unit and at least one nucleic acid capturing unit connected via a flow channel, (2) plural first liquid flow channels that are connected to the plural reaction chambers in a one-on-one relationship on a first surface side, and (3) a second liquid flow channel that is commonly connected to the plural reaction chambers on a second surface side opposite to the first surface.

Furthermore, one aspect of the single cell analysis apparatus of the present invention for solving the above problem is a single cell analysis apparatus, including (1) a stage on which a flow cell device for single cell analysis is placed, the flow cell device for single cell analysis including (1-1) plural reaction chambers each including at least one cell capturing unit and at least one nucleic acid capturing unit connected via a flow channel, (1-2) plural first liquid flow channels connected to the plural reaction chambers in a one-on-one relationship on a first surface side, (1-3) a second liquid flow channel that is commonly connected to the plural reaction chambers on a second surface side opposite to the first surface, (2) a stage controlling system for controlling the position of the stage, (3) an introduction controller for individually controlling introductions of a first liquid to the plural first fluid flow channels, (4) a discharge controller for controlling discharge of a second liquid from the second fluid flow channel.

Advantageous Effects of Invention

According to the present invention, a simultaneous one-by-one analysis of a large number of cells can be realized in an inexpensive and easy manner. Problems, configurations, and effects other than those mentioned above will be apparent from the following explanation of the embodiments.

DESCRIPTION OF EMBODIMENTS

Figure 1:
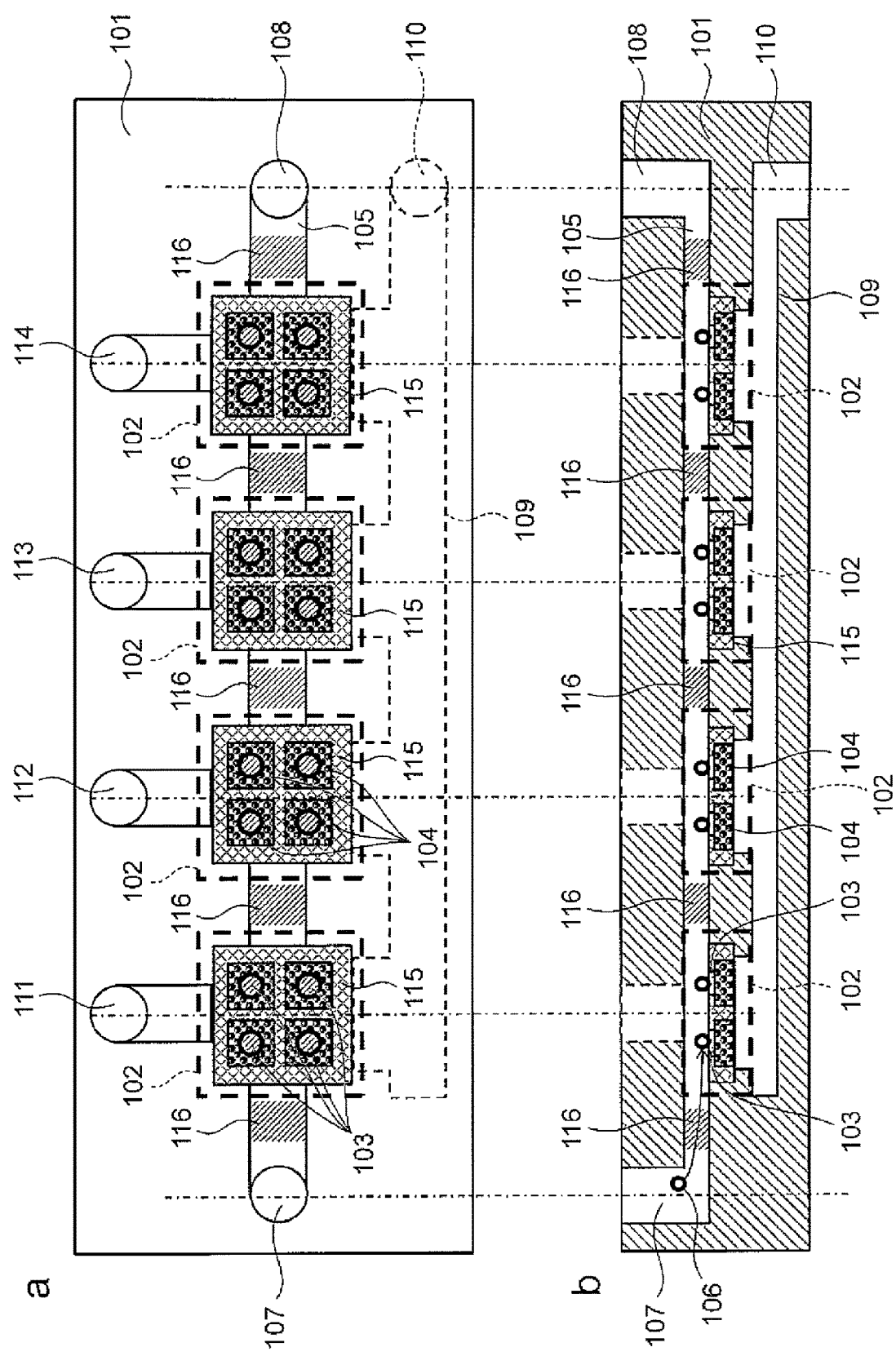
FIG. 1 shows diagrams of a basic configuration of a flow cell device according to a mode example.

Hereinunder, embodiments of the present invention will be described with reference to the drawings. Incidentally, the embodiments of the present invention are not limited to the mode examples described below, and various modifications may be made in the scope of the technical idea.

Summary of Embodiments

Prior to explaining concrete mode examples, a basic configuration and a basic concept adopted in the mode examples are explained. In each mode example, a flow cell device having a structure that can implement two processes essential for a single cell analysis (isolation of a cell, and preparation of a sample from the isolated individual cell) and process operations of a single cell analysis apparatus using the flow cell device will be explained.

The two processes essential for a single cell analysis can be implemented in one flow cell device, whereby manual operations for dispensing reagents are avoided, and the volumes of the reagents required are reduced and a running cost required for the single cell analysis is reduced. In addition, the entire process of the single cell analysis can be automated (reaction treatments essential for each cell can be automated), whereby simplification of a sample preparation process required for a large scale sequencer is realized, and even a person other than a veteran engineer can easily perform a single cell analysis.

Furthermore, we decided to apply the membrane device disclosed in PTL 3 in which a cell identification sequence is immobilized in a sample preparation from mRNAs extracted from a cell to build up a flow cell device of a mode example. By this, for a large number of cells, a $1^{st}$ cDNA library can be simultaneously built up in a high efficient manner from a large number of cells, and at the same time, a uniform sample preparation can be realized with small amounts of reagents per cell. That is, it is possible to prepare a sample for a large scale sequence analyzer (next generation sequencer) that can be subjected to a gene expression analysis for each individual cell. Thus, a sequencing library can be inexpensively built up.

In addition, in the following embodiments, a method is explained in which, in a sample preparation reaction of a flow cell device, the process can be performed using a considerably smaller number of kinds of cell identification tags as compared with the cell number in the flow cell device. The method is a method in which plural membrane devices having an identical combination of cell identification tags are placed in the flow cell device (for example, 20 membrane devices having 100 kinds of identification tags is placed in flow cell devices), and in a reaction after a $2^{nd}$ cDNA synthesis, a tag sequence that can identify a different membrane device is inserted into a nucleic acid sample for sequencing.

By this method, the number of cells that can be processed in one flow cell device can be increased to a number calculated as the product of the number of kinds of the cell identification tags on one membrane device and the number of kinds of the tag sequences for identifying the membrane device. That is, by providing sequences of the number of kinds that is calculated as the sum of the number of kinds of the cell identification tags and the number of kinds of the tag sequences for identifying the membrane device, cells of a number up to the number calculated as the product of the tag numbers can be identified. When this method is realized on the flow cell device according to the mode example, the reagent amounts per cell can be reduced to reduce the reagent cost.

In one of the following mode examples, described is a flow cell device for single cell analysis including: (1) plural reaction chambers each including at least one pair of a cell capturing unit and a nucleic acid capturing unit; (2) a first liquid flow channel that is commonly connected to the plural reaction chambers to introduce a first liquid into the plural reaction chambers; (3) plural second liquid flow channels that are connected to the plural reaction chambers in a one-on-one relationship to individually introduce a second liquid into the respective reaction chambers; and (4) a third liquid flow channel that is commonly connected to the plural reaction chambers to recover the first liquid and/or the second liquid that has passed through the cell capturing unit and the nucleic acid capturing unit.

In addition, in one of the following mode examples, described is a flow cell device for single cell analysis, including: (1) plural reaction chambers each including at least one pair of a cell capturing unit and a nucleic acid capturing unit, (2) plural first liquid flow channels that are connected to the plural reaction chambers in a one-on-one relationship to individually introduce a liquid to the respective reaction chambers; and (3) a second liquid flow channel that is commonly connected to the plural reaction chambers to recover the liquid that has passed through the cell capturing unit and the nucleic acid capturing unit.

[Configuration of Flow Cell Device]

FIG. 1 shows a top view (FIG. 1(*a*)) and a cross section (FIG. 1(*b*)) of a flow cell device. A flow cell device 101 is provided with plural reaction chambers 102. One or plural cell capturing units 103 and one or plural nucleic acid capturing units 104 are disposed on each of the reaction chambers 102. The nucleic acid capturing units 104 are desirably disposed in a one-on-one relationship to the cell capturing units 103. With the one-on-one configuration, the correspondence relationship of one cell captured by the cell capturing unit 103 with nucleic acids captured by the nucleic acid capturing unit 104 is clarified. In the case of FIG. 1, the nucleic acid capturing unit 104 is laminated with the cell capturing unit 103 on the lower surface side of the cell capturing unit 103. With the lamination relationship, nucleic acids extracted from one cell captured in the cell capturing unit 103 can be securely introduced into the corresponding nucleic acid capturing unit 104.

The flow cell device 101 shown in FIG. 1 includes in a base plate a common supply flow channel 105 connected to the plural reaction chambers 102 on the upper surface side thereof and a common suction flow channel 109 connected to the plural reaction chambers 102 on the lower surface side thereof. In the common supply flow channel 105, a solution containing cells 106 to be subjected to the test flows. The solution is introduced from an upper common inlet 107 provided in the common supply flow channel 105, flows along the common supply flow channel 105, and is recovered from an upper common outlet 108. During this time, the solution fills the reaction chambers 102 which are positioned on the common supply flow channel 105.

At the same time with the solution introduction, a negative pressure is applied to a lower common outlet 110 provided in the common suction flow channel 109. When the common suction flow channel 109 is under a negative pressure, a part of the solution filling the reaction chamber 102 flows through the cell capturing unit 103 and the nucleic acid capturing unit 104 into the common suction flow channel 109. The cell capturing unit 103 is configured to have an opening smaller than the diameter of the cell 106. Thus, the cell 106 can be captured by the opening of the cell capturing unit 103. Just under the cell capturing unit 103, the nucleic acid capturing unit 104 made of a porous material is disposed. The cell capturing unit 103 and the nucleic acid capturing unit 104 are fabricated on a two-dimensional array chip 115 which is disposed in each of the reaction chambers 102 in a one-on-one relationship. In the case of FIG. 1, four structures, each of which is composed of one pair of the cell capturing unit 103 and the nucleic acid capturing unit 104, are disposed at prescribed positions in each of the reaction chambers 102.

As a result, the cells 106 are captured uniformly by the plural cell capturing units 103 on the plural two-dimensional array chips 115 disposed in the plural reaction chambers 102. For making it possible to subject the captured cells 106 to different treatments from one reaction chamber 102 to another, an individual fluid flow channel different from the common supply flow channel 105 is connected to each of the reaction chambers 102. The fluid channels are connected to the reaction chambers 102 in a one-on-one relationship. In FIG. 1, four fluid channels and the respective four individual inlets 111, 112, 113, and 114 are shown. An individual reagent is introduced to each of the individual inlets 111, 112, 113, and 114 according to each treatment to be implemented in the connected reaction chamber 102. In the case of FIG. 1, the individual fluid channel is connected on the upper surface side of each of the reaction chambers 102 from the lateral side thereof.

When a reagent is individually introduced into each reaction chamber 102, the reverse flow of the individual reagent is prevented by applying a negative pressure to the common suction flow channel 109 connected to the lower surface side of the reaction chamber 102 while stopping the flow of the solution in the common supply flow channel 105. By this, the possibility that the individually introduced reagent is introduced to any other reaction chamber 102 than the introduction target can be sufficiently reduced.

From the viewpoint of surely preventing the erroneous introduction of the individually introduced reagent to any other reaction chamber 102 than the introduction target, a common supply flow channel 105 in which inner walls of areas 116 between one reaction chamber 102 and the next reaction chamber 102 or before or after one reaction chamber 102 have been subjected to a water repellant (hydrophobic) treatment is used, and prior to the introduction of the individual reagents, a non-polar solvent such as a mineral oil may be allowed to flow from the upper common inlet 107 toward the upper common outlet 108. In this case, the non-polar solvent remains in the areas 116 in the common supply flow channel 105, thereby allowing the reaction chambers 102 to be in the state of being separated from each other. That is, an aqueous solution which is a polar solvent can not pass through the areas 116, and the introduction of the individual introduced reagent to any other reaction camber 102 does not occur.

As described above, when the flow cell device 101 shown in FIG. 1 is used, a common solution can be introduced at once into the plural reaction chambers 102 through the common supply flow channel 105, while individual reagents can be introduced into individual reaction chambers 102 through individual fluid channels. Accordingly, by using the flow cell device 101 shown in FIG. 1, a highly precise gene expression analysis can be implemented simultaneously for a large number of cells. In addition, in a reaction process that does not require the individual introductions of the reagents (reaction liquids), an identical reaction process can be implemented in the plural reaction chambers 102, and uniform reaction among the reaction chambers 102 can be achieved and a highly precise analysis is realized.

[First Regulation Method of Sequencing Library]

Hereinunder, a first method for a sequencing a sample preparation library from a large number of cells in one sequence analysis will be explained.

As described above, the flow cell device 101 (FIG. 1) is provided with the plural reaction chambers 102, and each of the reaction chambers 102 is provided with the two-dimensional array chip 115 on which plural structures each composed of a pair of the cell capturing unit 103 for isolating and capturing each cell from multiple cells and the nucleic acid capturing unit 104 made of a porous material are disposed in a planar form.

Figure 2:
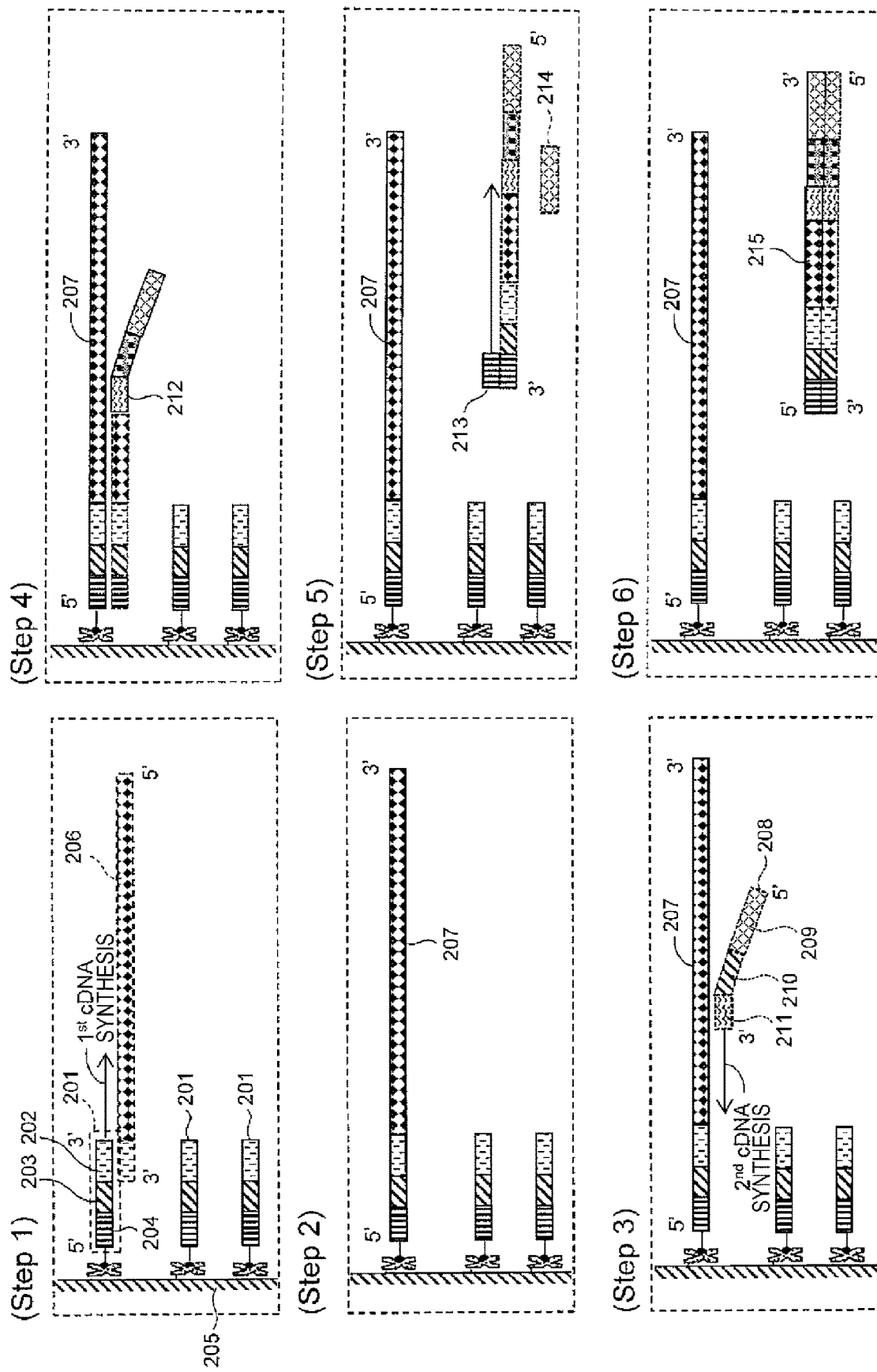
FIG. 2 shows reaction course diagrams for explaining a first regulation method of a sequencing library.

FIG. 2 shows enlarged structures of an inner wall surface (surface of the porous material) of the nucleic acid capturing unit 104. As shown in FIG. 2, to the inner wall surface of the nucleic acid capturing unit 104, a first DNA probe 201 is immobilized. The first DNA probe 201 includes a capturing sequence (poly-T) 202 for capturing a nucleic acid (mRNA) 206 extracted from a cell captured by the cell capturing unit 103, a known sequence (cell identification sequence) 203 for identifying a cell 106, and a common sequence 204 for PCR amplification.

(Step 1)

This step shows a state where the mRNA 206 is captured by the capturing sequence 202 of the first DNA probe 201. Incidentally, when different nucleic acid capturing units 104, if present in the same reaction chamber 102, are disposed at different positions in the reaction chamber 102, different cell identification sequences 203 are attached. For example, in the case of the structure of FIG. 1, to each of the four nucleic acid capturing units 104 constituting the two-dimensional array chip 115, a unique cell identification sequence 203 is attached according to the disposed position. The nucleic acid 206 is taken out from the cell 106 captured by the cell capturing unit 103 by crushing the cell 106 by electrophoresis or flow of a solution.

(Step 2)

This step shows a state where a $1^{st}$ cDNA strand 207 is synthesized using mRNA 206 captured on the first DNA probe 201 as a template. A reverse transcriptase and substrates required for the synthesis reaction are supplied according to the following procedure. First, a buffer solution containing the enzyme and the substrates is allowed to flow from the upper common inlet 107 toward the upper common outlet 108 to fill the top space of the two-dimensional array chip 115 present in each of the reaction chambers 102 with the buffer solution. Next, a negative pressure is applied to the lower common outlet 110 to allow the solution in the reaction chamber 102 to flow into the common suction flow channel 109 so as to pass through the nucleic acid capturing unit 104, thereby filling the vicinity of the surface of the porous material with the necessary reagent.

(Step 3)

In this step, a second DNA probe 208 that hybridizes to a prescribed position from the cell identification sequence 203/region (for example, around 200 bases therefrom/region of 150 to 250 bases) is introduced independently for each reaction chamber 102. The step 3 of FIG. 2 shows a state where the second DNA probe 208 hybridizes to the $1^{st}$ cDNA strand 207. The second DNA probe 208 is composed of, from the 5' end, a common primer (Forward) 209 for PCR, a chip identification sequence 210, and a gene specific probe 211 which is a sequence complementary to the $1^{st}$ cDNA strand 207. Here, the chip identification sequence 210 has a different sequence from one reaction chamber 102 to another (That is, from one two-dimensional array chip 115 to another). In addition, the required number of the gene specific probes 211 is a number for acquiring gene expression data, and if 20 kinds of gene expression analyses are conducted, a mixed solution of 20 kinds of gene specific probes 211 is to be introduced to the reaction chamber 102.

The introduction of the second DNA probes 208 into the reaction chambers 102 is performed according to the following procedure. First, a mineral oil is introduced from the upper common inlet 107, passes through the common supply flow channel 105, and is discharged from the upper common outlet 108 on the opposite side. In this stage, the four reaction chambers 102 connected to the common supply flow channel 105 are not separated yet. Next, a buffer solution containing a salt is allowed to flow from the common suction flow channel 109 toward the individual inlets 111, 112, 113, and 114, and the excess mineral oil present in the individual reaction chambers 102 is discharged through the individual inlets 111, 112, 113, and 114. After the discharge, the mineral oil remains only in the areas 116. As a result, the four reaction chambers 102 connected to the common supply flow channel 105 are separated from each other. That is, the top space of the two-dimensional array chip 115 provided in one reaction chamber 102 is separated from the top space of the two-dimensional array chip 115 provided in another reaction chamber 102.

This separation occurs because, while the inner wall of the reaction chamber 102 defining the top space of the two-dimensional array chip 115 has been surface-treated so as to be hydrophilic, the area 116 positioned between the reaction chambers 102 has been surface-treated to be hydrophobic. It is important for maintaining a high reaction efficiency that the $1^{st}$ cDNA probe 201 is immobilized strongly (for example, by a biotin-avidin bond) to the inner wall surface of the nucleic acid capturing unit 104 (the surface of the porous material).

After the separation of the reaction chambers 102 is completed, buffer solutions containing the second DNA probes 208 having different chip identification sequences 210 are introduced into the reaction chambers 102 through the individual inlets 111, 112, 113, and 114, and the introduced buffer solutions are discharged from the lower common outlet 110 through the cell capturing units 103, the nucleic acid capturing units 104, and the common suction flow channel 109. Thus, the vicinity of the inner wall of the nucleic acid capturing unit 104 is filled with the second DNA probes 208 different for each reaction chamber 102, and the second DNA probe 208 is hybridized to the $1^{st}$ cDNA strand 207.

(Step 4)

In this step, a $2^{nd}$ cDNA 212 is synthesized. For introducing substrates and an enzyme required for this reaction, first, a large amount of a buffer solution is allowed to flow from the upper common inlet 107 toward the upper common outlet 108. By the large amount of the buffer solution, an emulsion oil remaining in the areas 116 is flushed. Since the purpose of allowing the large amount of the buffer solution to flow in the common supply flow channel 105 is to open inside the common supply flow channel 105 again, a small amount of the emulsion oil may remain in the areas 116. Next, by the same process as in the $1^{st}$ cDNA synthesis, the enzyme and substrates required for the $2^{nd}$ cDNA synthesis are introduced into the reaction chambers 102.

(Steps 5 and 6)

In the steps, PCR amplification by a common primer 214 is conducted. The common primer (Forward) 214 and a common primer (Reverse) 213 required for the PCR amplification, a PCR enzyme, and substrates are introduced into the reaction chambers 102 by the same procedure as in the case of the $1^{st}$ cDNA strand 207. PCR products 215 obtained after completing the reaction, each of which has a sequence that can be analyzed for the sequence (strictly speaking, a sequence for which a pretreatment of the sequence analysis (emulsion PCR, etc.) can be performed), are referred to as a sequencing library.

By subjecting the sequencing library to sequence analysis, the gene expression level can be obtained for each cell identification sequence (the cell identification sequence 203) and each chip identification sequence (the chip identification sequence 210). That is, a number of cells that is equal to or less than the number calculated as the product of the number of kinds of the cell identification sequences 203 simultaneously introduced in the flow cell device 101 and the number of kinds of the chip identification sequences 210 can be analyzed at the same time. By this, a considerably larger number of cells can be analyzed than the number of the cell identification sequences previously introduced into the two-dimensional array chip 115.

[Second Regulation Method of Sequencing Library]

However, in the above method, when the number of genes to be analyzed is large, the number of kinds of the second DNA probes 208 required to be provided is a number calculated as the number of kinds of the chip identification sequences 210×the number of genes to be analyzed. For this reason, a large amount of the second DNA probes 208 have to be provided. Thus, hereinunder, a second method for solving the problem will be explained.

In the second method, the chip identification sequences 210 are introduced not in the synthesis of the $2^{nd}$ cDNAs 212 but in the primary process of the PCR amplification after synthesis of the $2^{nd}$ cDNAs. With this way, the above problem (that is, the problem that, when the number of genes to be analyzed is large, the number of kinds of the second DNA probes 208 to be provided increases by the product of the chip number and the gene number) can be avoided.

Figure 3:
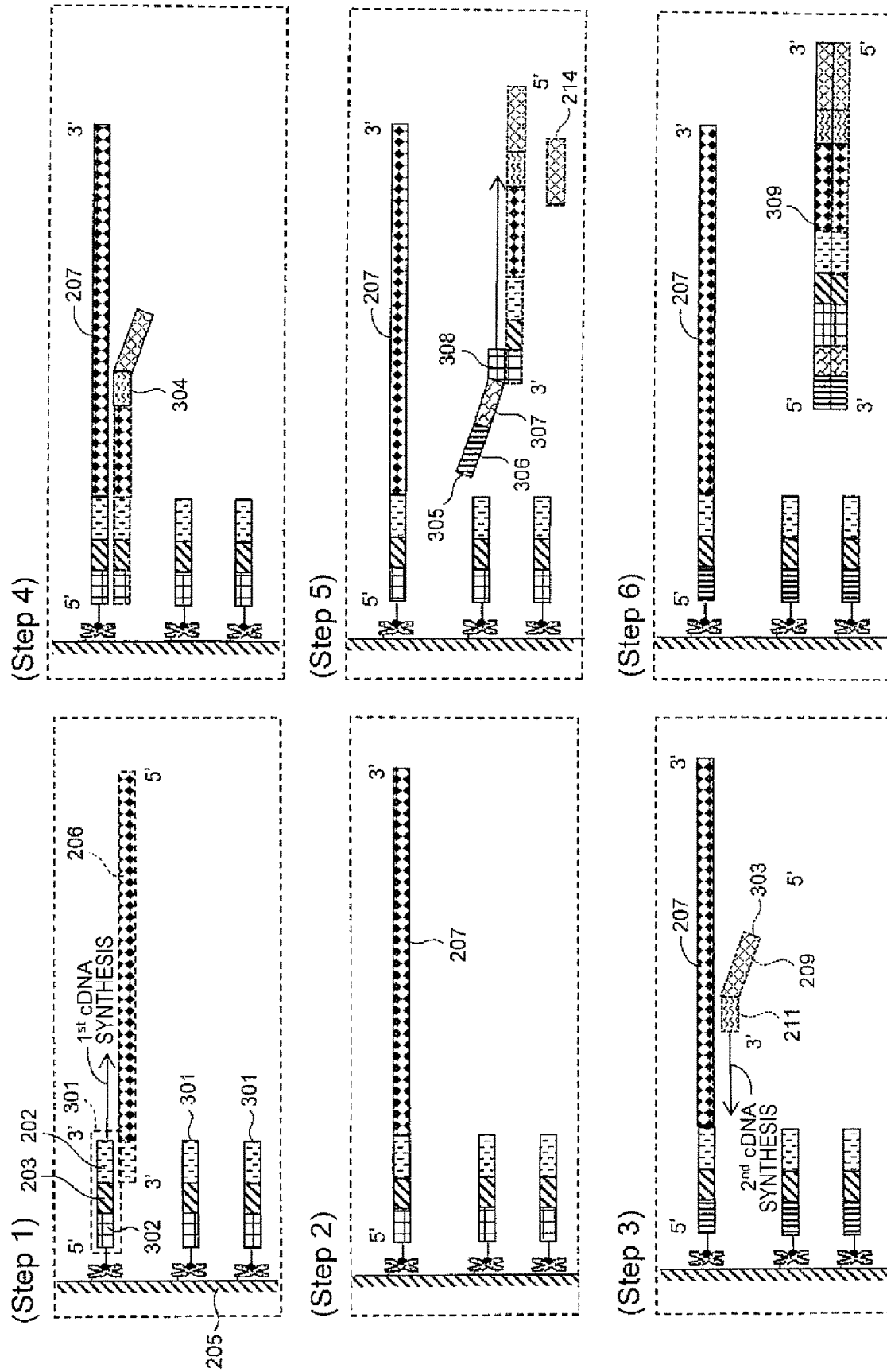
FIG. 3 shows reaction course diagrams for explaining a second regulation method of a sequencing library.

Hereinunder, with reference to FIG. 3, the points in which the nucleic acid treatment process is different from the first method are explained. FIG. 3 shows the entire process until a sequencing library is obtained, like in FIG. 2.

(Steps 1 and 2)

A sequence of a first DNA probe 301 immobilized on the inner wall surface of nucleic acid capturing unit 104 is provided with a common connection sequence 302 instead of the common sequence 204 (common PCR primer (Reverse)).

(Step 3)

A second DNA probe 303 in synthesis of the $2^{nd}$ cDNA has a sequence obtained by removing the chip identification sequence 210 from the sequence of the second DNA probe 208 (FIG. 2). That is, the second DNA probe 303 is composed only of the common primer (Forward) 209 and the gene specific probe 211.

(Step 4)

The second DNA probe 303 is hybridized to the $1^{st}$ cDNA strand 207 to synthesize a $2^{nd}$ cDNA strand 304.

(Step 5)

To the synthesized $2^{nd}$ cDNA strand 304, a third DNA probe 305 having a second chip identification sequence 307 is hybridized. The third DNA probe 305 is composed of a PCR common primer (Reverse) 306, the second chip identification sequence 307, and a complementary sequence 308 of the common connection sequence.

(Step 6)

As PCR amplification products 309 obtained after the completion of the PCR process, a sequencing library is built. Since the number of kinds of the third DNA probes 305 may be the same as the number of the chips, the initial cost for the DNA probes can be reduced to increase the number of cells that can be simultaneously analyzed.

Example 1

(Structure of Flow Cell Device)

Hereinunder, one of examples which are concrete configurations of the aforementioned mode examples will be explained. In the Example, a large number of beads having DNAs (DNA probes) for capturing nucleic acids immobilized on the surface thereof are packed to configure the nucleic acid capturing unit 104. In addition, in the case of the Example, a sequencing library is regulated based on the aforementioned first method.

Figure 4:
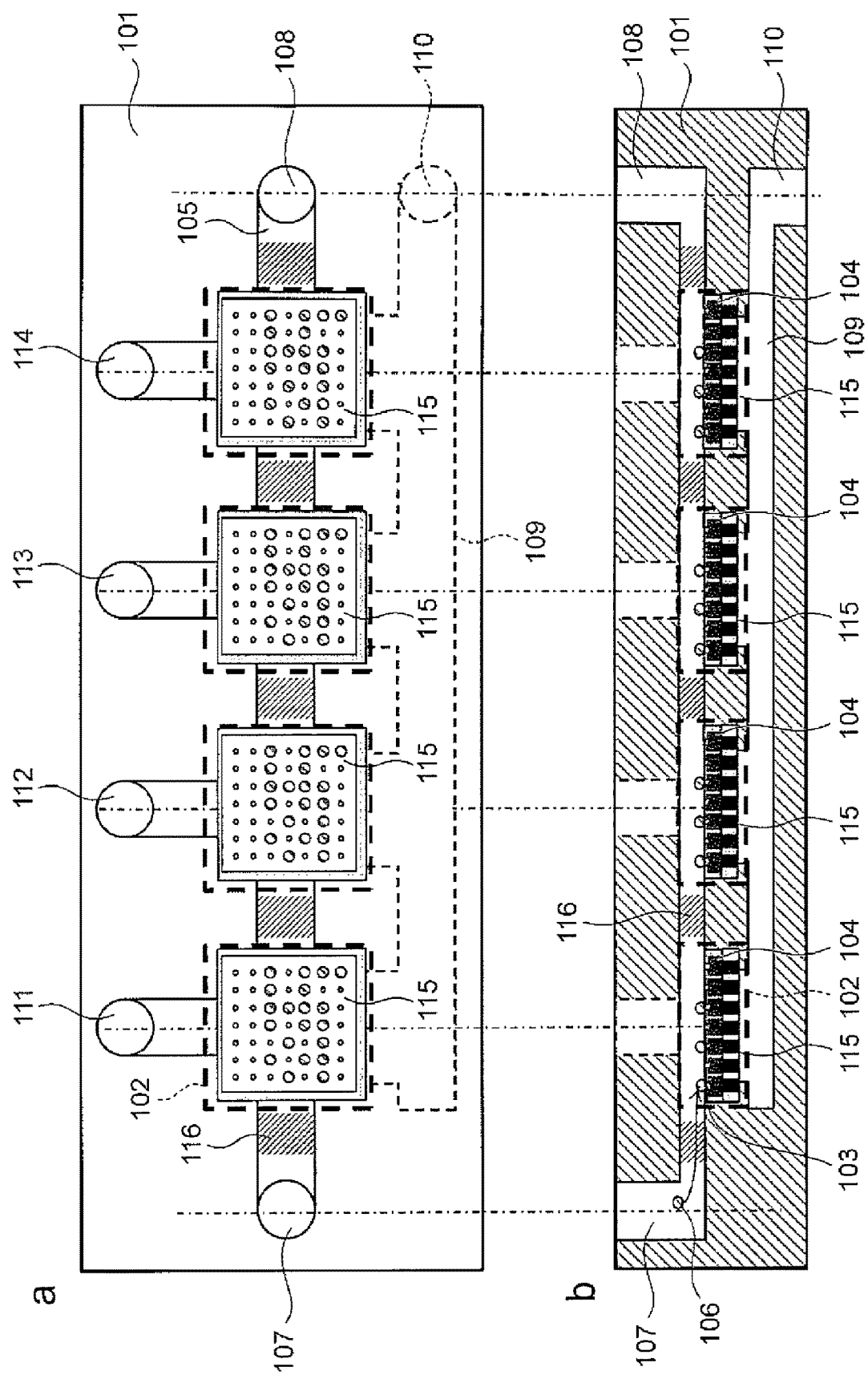
FIG. 4 shows diagrams of a configuration of a flow cell device according to Example 1.

FIG. 4 shows a top view (FIG. 4(a)) and a cross section (FIG. 4(b)) of the flow cell device 101 used in the Example. A basic structure of the flow cell device 101 in the Example is the same as the basic structure of FIG. 1. That is, the flow cell device 101 includes four reaction chambers 102, each of which includes one or plural cell capturing units 103 and nucleic acid capturing units 104. The nucleic acid capturing units 104 are desirably disposed in a one-on-one relationship to the cell capturing units 103. In FIG. 4, the nucleic acid capturing units 104 are disposed in a one-on-one relationship to 7×7 of the cell capturing units 103 formed in the two-dimensional array chip 115.

Also in the case of the Example, the nucleic acid capturing unit 104 is disposed just under the cell capturing unit 103. However, in the case of the Example, the nucleic acid capturing unit 104 is formed by a space filled with a large number of magnetic beads. Also in the case of the Example, a solution containing the cells 106 is introduced from the common inlet 107. The introduced solution flows along the common supply flow channel 105 sequentially to the four reaction chambers 102, and finally, discharged from the upper common outlet 108. When the solution is allowed to flow in the common supply flow channel 105, by controlling the common suction flow channel 109 formed under the reaction chambers 102 under a negative pressure, the solution in the common supply flow channel 105 partially flows through the reaction chambers 102 into the common suction flow channel 109.

By this flow, the cells 106 in the solution are attracted to the openings each configuring the cell capturing unit 103 and captured. In this time, one cell 106 is captured by one cell capturing unit 103. In addition, by this flow, the captured cell 106 is broken, and mRNAs are extracted from the cell 106 and captured onto the surface of the magnetic beads in the nucleic acid capturing unit 104. In this manner, in the Example, a cDNA library is built in the nucleic acid capturing unit 104 formed at the same position as the cell capturing unit 103. With the library as templates, $2^{nd}$ cDNAs are synthesized using DNA probes having a different sequence for each two-dimensional array chip 115 to build a sequencing library.

Figure 5:
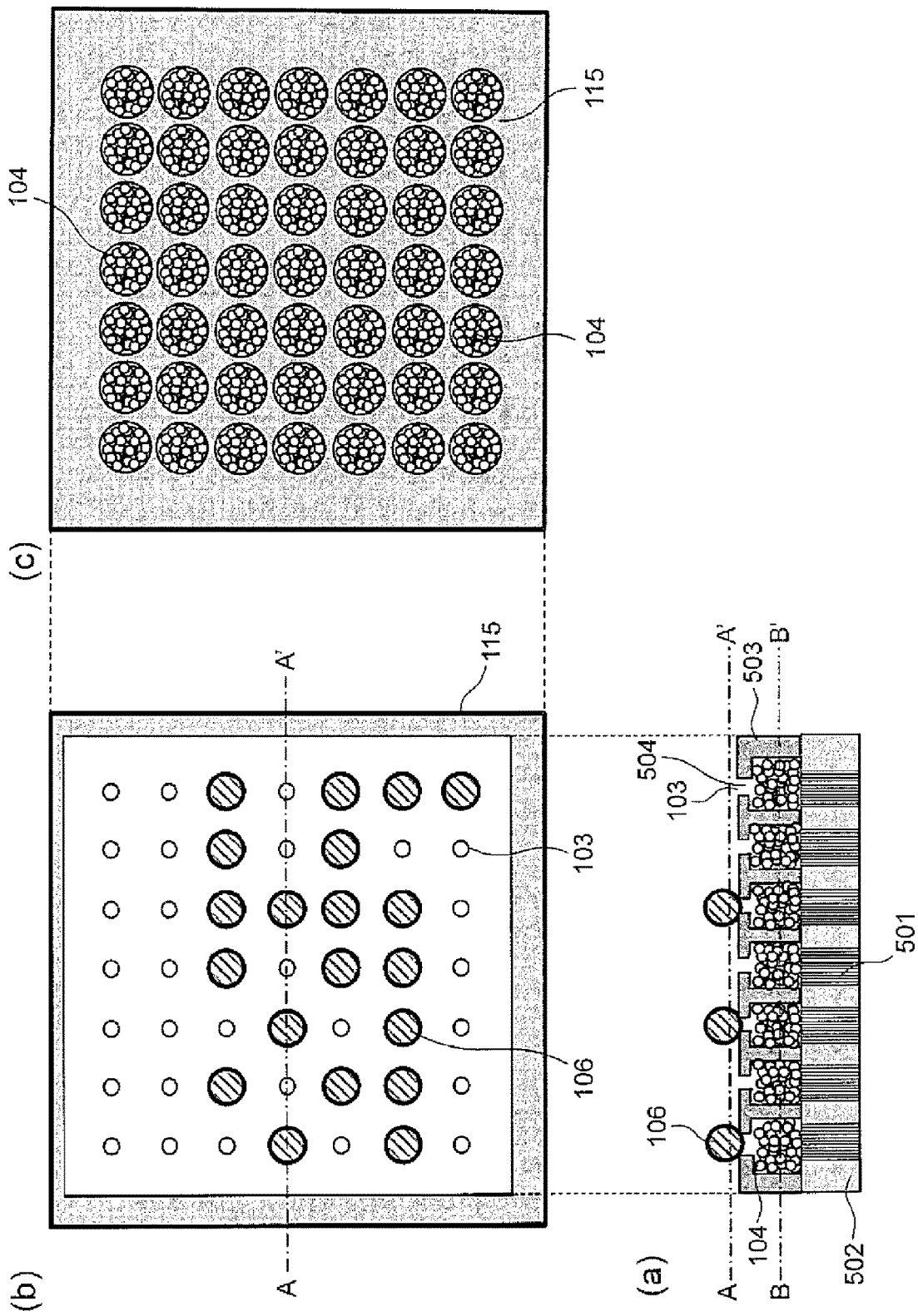
FIG. 5 shows diagrams of a configuration of a two-dimensional array chip used in Example 1.

FIG. 5 shows a detailed configuration of the two-dimensional array chip 115 used in the Example. FIG. 5(a) is a cross section perpendicular to the surface of the two-dimensional array chip 115. FIG. 5(b) is an A-A' cross-section of FIG. 5(a) viewed from the upper surface side, and FIG. 5(c) is a B-B' cross-section of FIG. 5(a) viewed from the upper surface side. The cell capturing unit 103 corresponds to the individual opening (flow channel 504) formed on the upper surface side of a chip 503, and the nucleic acid capturing unit 104 corresponds to a large number of the magnetic beads 601 accommodated in the space surrounded by the chip 503 and a pore array sheet 502.

Figure 6:
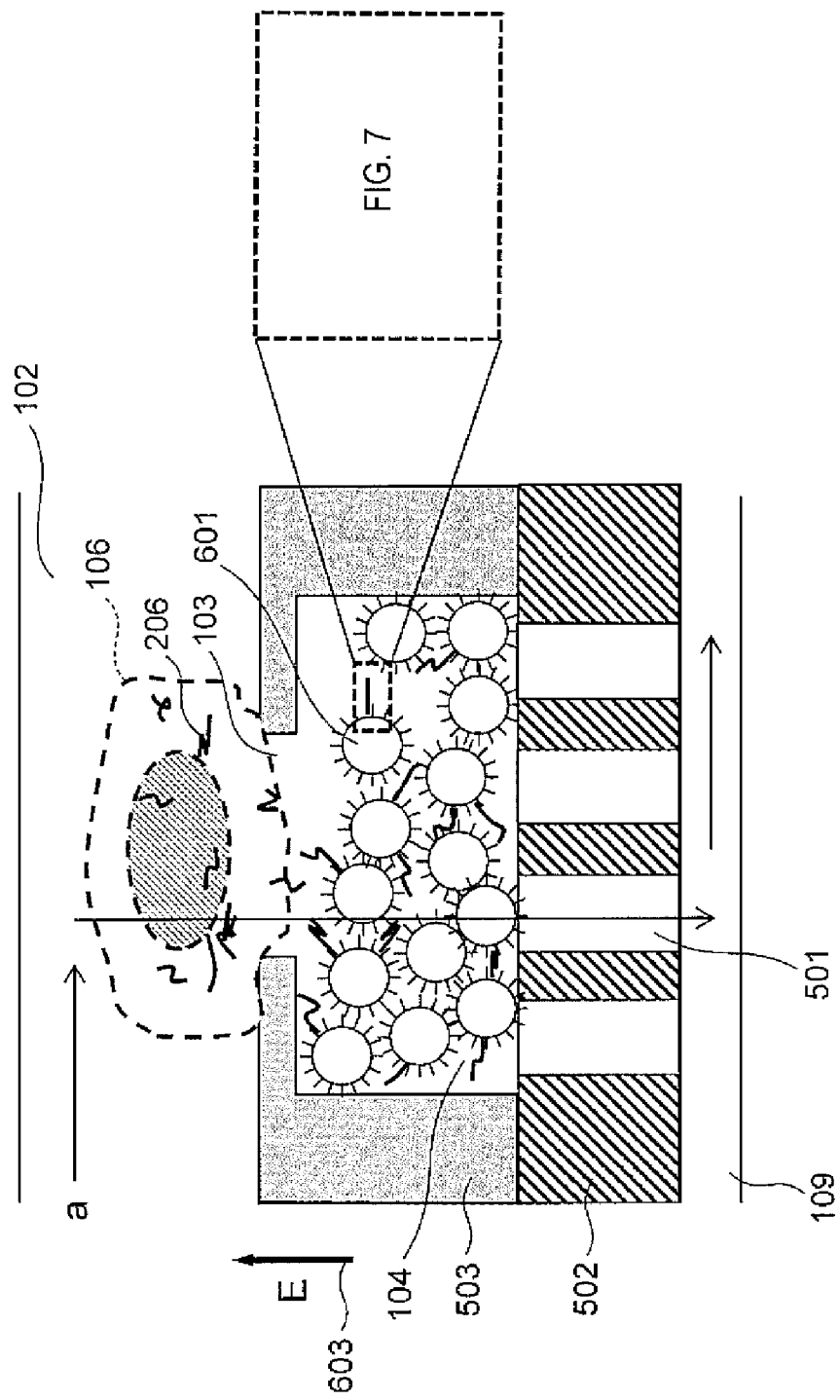
FIG. 6 shows an enlarged view of a unit structure of the two-dimensional array chip used in Example 1.

FIG. 6 shows an enlarged view of a unit structure of the two-dimensional array chip 115 (FIG. 5). As shown in FIG. 6, the unit structure is composed of a pair of the cell capturing unit 103 and the nucleic acid capturing unit 104 in which a large number of magnetic beads 601 are packed, and a pore array sheet 502 in which lower flow channels 501 are formed. The pore array sheet 502 functions as a member that closes a large number of recessed portion formed on the lower surface side of the chip 503 and encloses the magnetic beads 601 in the recessed portion. The flow channels 501 are a large number of through holes formed in the pore array sheet 502 and connect the nucleic acid capturing unit 104 with the common suction flow channel 109. The dimension of the lower flow channel 501 is formed into a dimension that can hold the magnetic beads 601 in the nucleic acid capturing unit 104.

(Single Cell Analysis Process: First Regulation Method)

Figure 7:
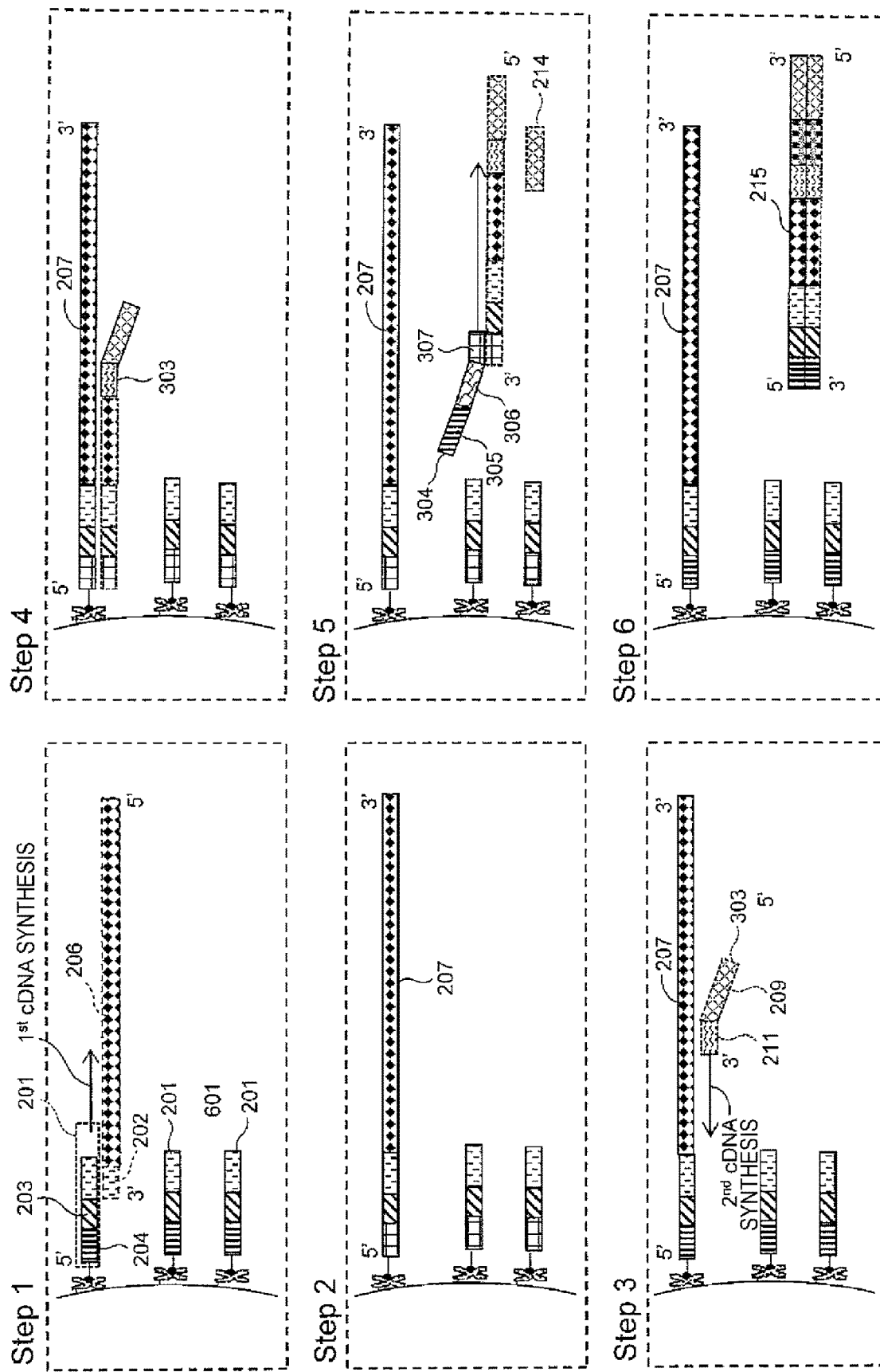
FIG. 7 shows diagrams of a reaction course implemented in Example 1.

A series of process steps implemented on the surface of the magnetic bead 601 will be explained with reference to FIG. 7. The following process corresponds to the first regulation method described above. FIG. 7 shows concept diagrams of the steps of: capturing a nucleic acid (mRNA) extracted from the cell 106 captured in the cell capturing unit 103 (Step 1); synthesizing a cDNA (Step 2); synthesizing a $2^{nd}$ strand in which a known terminal sequence required for nucleic acid amplification (PCR) and sequencing is introduced (Steps 3 and 4); and performing PCR amplification (Step 5,6). The steps 1 to 6 of FIG. 7 correspond to the steps 1 to 6 of FIG. 3.

(Step 1)

First, the cells 106 are washed with 500 μL of 1×PBS buffer (phosphate buffered saline) in a manner that does not damage the cell, then 1000 cells 106 suspended in 10 μL of 1×PBS buffer cooled to 4° C. are introduced from the common inlet 107 formed on the upper surface of the flow cell device 101 (FIG. 4). At the same time, the solution is sucked from the upper common outlet 108 which is the opposite side end of the common supply flow channel 105 so that the four reaction chambers 102 are filled with this solution. Thus, the upper portion of the two-dimensional array chip 115 disposed in each of the reaction chambers 102 is filled with the PBS buffer containing the cells 106.

Next, a negative pressure (1.0 atm) is applied on the lower common outlet 110 to suck the solution from the cell capturing unit 103 to the common suction flow channel 109 (FIG. 4). The cell 106 moves along the flow of the solution to reach the cell capturing unit 103. As shown in FIG. 5(b), since the diameter of the opening of the cell capturing unit 103 is smaller than the diameter of the cell 106, the reaching cell 106 is captured on the opening of the cell capturing unit 103. Since the captured cell 106 plays a role of a plug against the solution flow, the solution flow moves toward the cell capturing units 103 that have not captured any of the cells 106. Thus, a remaining cell 106 in the solution moves toward an opening that has not captured any of the cells 106 and is captured thereon.

After a sufficient number of the cells 106 are captured on the cell capturing units 103, the cells 106 remaining in the reaction chambers 102 (excess cells 106 that have not been captured yet) and the PBS buffer are discharged from the upper common outlet 108. Subsequently, a cell lysate (lysis buffer) (for example, a surfactant such as Tween 20) is allowed to flow from the upper common inlet 107 toward the upper common outlet 108 to fill the reaction chambers 102 with the cell lysate. Immediately after the reaction chambers 102 are filled with the cell lysate, a negative pressure is applied to the lower common outlet 110 to suck the cell lysate. All the solutions described below are allowed to pass through the nucleic acid capturing units 104 in the two-dimensional array chips 115 in the same manner. At this time, the lower flow channels 501 formed in the pore array sheet 502 are flow channels formed by a porous material having a diameter of 0.2 µm, and have a large pressure loss. For this reason, the cell lysate continuously flows from the reaction chambers 102 through the cell capturing units 103 and the nucleic acid capturing units 104 to the common suction flow channel 109 slowly over approximately 5 minutes.

The cell lysate crushes the cell 106 during flowing. Nucleic acids (mRNAs) 206 are extracted from the crushed cell 106. The nucleic acids 206 pass through the cell capturing unit 103 along with the cell lysate without spreading into the circumference to reach the nucleic acid capturing unit 104. Alternatively, an electric field may be applied in a direction shown by an arrow 603 (a direction from the lower surface side to the upper surface side of the flow cell device 101) to cause the nucleic acids 206 in the cell 106 to move to the nucleic acid capturing unit 104 by electrophoresis. By the introduction of the cell lysate, the crushing of the cell 106 and the capturing of the nucleic acids 206 by the first DNA probe 201 immobilized on the magnetic beads 601 in the nucleic acid capturing unit 104 are simultaneously implemented.

The positional information on the two-dimensional array chip 115 of the cell capturing unit 103 capturing the cell 106 (in the case of FIG. 5(a), information of: which position of cell capturing unit 103 among the cell capturing units 103 arranged in a 7×7 lattice form) is stored as a sequence information of the first DNA probe 201 immobilized on the magnetic bead 601 in the corresponding nucleic acid capturing unit 104. That is, in the first DNA probe 201 of the nucleic acid capturing unit 104, the capturing sequence 202 that is different for each position of the nucleic acid capturing unit 104 on the two-dimensional array chip 115 is introduced. The first DNA probe 201 has, not only the capturing sequence 202, but also a poly-A sequence on the 3' end thereof. The poly-T sequence on the 3' end side of the first DNA probe 201 is hybridized with a poly-A sequence on the 3' end of the nucleic acid 206 to thereby capture the nucleic acid 206. On the 5' end side of the first DNA probe 201, the common primer 204 (Reverse) for PCR amplification is further provided.

Incidentally, the first DNA probe 201 of the Example has a more complicate sequence configuration, and the common primer for PCR amplification 204 (Reverse) of 30 bases, the cell identification sequence 203 composed of a cell recognition sequence of 7 bases and a random sequence of 7 bases, and the capturing sequence 202 composed of an oligo (dT) sequence of 18 bases+a VN sequence of 2 bases are arranged in this order from the 5' end. Here, since the cell identification sequence is set as the random sequence of 7 bases, it is possible to recognize at most $4^7=1.6\times10^4$ single cells.

In addition, since $4^7=1.6\times10^4$ molecules can be recognized when a molecule recognition sequence (for example, 7 bases) is introduced into the first DNA probe 201, based on DNA sequence data of amplification products obtained with a next generation sequencer, it is possible to recognize which molecule some amplification products that are derived from the same cell and have the same gene sequence are derived from. That is, amplification bias among genes generated in the amplification step can be corrected. For this reason, the nucleic acids which have been initially present in the sample can be quantified in a highly precise manner. However, when the expression level of an identical gene in a single cell is higher than the variations of the molecule recognition sequences, the precision of the amplification bias correction is lowered. The oligo (dT) sequence positioned on the most 3' end side is hybridized with the poly-A tail added on the 3' side of the nucleic acid 206, and utilized for capturing the nucleic acid 206.

In the Example, although a poly-T sequence is used as a part of the first DNA probe 201 for analyzing the mRNA, for performing a micro-RNA analysis and a genome analysis, instead of the poly-T sequence, a random sequence or a part of a sequence complementary to the sequence to be analyzed may obviously be used.

(Step 2)

With the nucleic acid 206 captured by the first DNA probe 201 as a template, a $1^{st}$ cDNA strand is synthesized. As a $1^{st}$ cDNA strand synthesis reagent, 58.5 µL of 10 mM Tris Buffer (pH=8.0) containing 0.1% Tween 20, 4 µL of 10 mM dNTP, 225 µL of 5×RT Buffer (SuperScript III, Invitrogen), 4 µL of 0.1 MDTT, 4 µL of RNase OUT (Invitrogen), and 4 µL of Superscript III (reverse transcriptase, Invitrogen) are blended and introduced from the upper common inlet 107 in the same manner as in the previous step. While allowing the solution to flow very slowly from the reaction chambers 102 into the common suction flow channel 109 in a state where the void space among the packed magnetic beads 601 is filled with a solution containing a reverse transcriptase and synthesis substrates, the solution is slowly heated to 50° C. to effect a complementary strand synthesis reaction (synthesis reaction of a $1^{st}$ cDNA strand) for 50 minutes.

As a result, for each cell 106, many cDNAs immobilized on the surface of the magnetic beads 601 are obtained as a library. This is a so-called one cell cDNA library array, and is fundamentally different from an averaged cDNA library which has hitherto been obtained from many cells.

After the completion of the reaction (after the $1^{st}$ cDNA strand is synthesized), the entire flow cell device 101 is kept at a temperature of 85° C. for 1.5 minutes to deactivate the reverse transcriptase. Furthermore, the entire flow cell device 101 is cooled to 4° C. Then, 0.2 mL of 10 mM Tris Buffer (pH=8.0) containing RNase and 0.1% Tween 20 is injected from the upper common inlet 107, and simultaneously sucked from the upper common outlet 108 on the opposite side to fill the reaction chambers 102 with the solution, and then, while the solution is discharged from the lower common outlet 110, the solution in the reaction chambers 102 is simultaneously removed from the upper common outlet 108. This procedure is repeated five times. Thus, the RNAs are degraded, and the residual matter and the degradation products in the nucleic acid capturing unit 104 are removed and the nucleic acid capturing unit 104 is cleaned. Furthermore, the nucleic acid capturing unit 104 is washed five times in the same manner with a liquid containing an alkali denaturation agent and a washing liquid. By the above process, a cDNA library array for each captured cell is built.

(Steps 3 and 4)

Next, 69 µL of sterilized water, 10 µL of 10×Ex Taq Buffer (TaKaRa Bio), 100 µL of 2.5 mM dNTP Mix, and 1 µL of Ex Taq Hot start version (TaKaRa Bio) having 10 µM of a common sequence for PCR amplification (Reverse) added are blended and the mixed reagent is introduced from the upper common inlet 107 through the common supply flow channel 105 into the nucleic acid capturing units 104 in the same manner as in the previous step. The individual introduction method of 10 μL of a mixed solution of 20 kinds of the second DNA probes 208 with a chip identification tag will be described later. Then, a secondary structure of the nucleic acid is loosened at 95° C. for 3 minutes and then, with the $1^{st}$ cDNA strand 207 as a template, a gene specific sequence of a primer is annealed at 44° C. for 2 minutes. FIG. 7 shows a state where the second DNA probe 208 is hybridized to the $1^{st}$ cDNA strand 207. The temperature is further elevated to 72° C. to effect a complementary strand extension reaction for 6 minutes and synthesize the $2^{nd}$ cDNA strand 304.

A mixed solution of 20 kinds of the second DNA probes 208 each having a different sequence in the region of the gene specific probe 211 (a solution in which a chip identification sequence have a different sequence from one reaction chamber 102 to another (that is, from one two-dimensional array chip 115 to another)) is introduced for each two-dimensional array chip 115 (reaction chamber 102). For the introduction, the individual inlets 111, 112, 113, and 114 are used as described later. A number of the gene specific probes 211 for which the gene expression data are to be obtained is required, and when expressions of 200 kinds of genes are analyzed, a mixed solution of 200 kinds of gene specific probes 211 is introduced into the reaction chambers 102.

Hereinunder, a method for introducing the second DNA probes 208 into the reaction chambers 102 will be explained. First, a mineral oil is introduced from the upper common inlet 107, and discharged from the upper common outlet 108. Next, a buffer solution containing a salt is allowed to flow from the common suction flow channel 109 toward the individual inlets 111, 112, 113, and 114, and the excess mineral oil in the reaction chambers 102 is discharged. By this, the reaction chamber 102 above the two-dimensional array chip 115 is separated from other reaction chambers 102 by the mineral oil remaining in the common supply flow channel 105. The separation is possible because the inner walls of the reaction chambers 102 above the two-dimensional array chips 115 have been surface-treated so as to be hydrophilic, whereas the areas 116 of the common supply flow channel 105 connected to the reaction chambers 102 have been surface-treated so as to be hydrophobic.

It is important for maintaining high reaction efficiency that the $1^{st}$ cDNA strands 207 are immobilized strongly (for example, by a biotin-avidin bond) on the porous inner walls. When the separation of the reaction chambers 102 is completed, buffer solutions each containing second DNA probes 208 having a different chip identification sequence are introduced from the individual inlets 111, 112, 113, and 114, passes through the common suction flow channel 109, and is discharged from the lower common outlet 110. By this, the vicinity of the inner wall of the nucleic acid capturing unit 103 is filled with second DNA probes 208 different from one reaction chamber 102 to another, and the probes can be hybridized to the $1^{st}$ cDNA strands 207.

The chip identification tag in the second DNA probe 208 is a random sequence of 4 bases as with the cell identification tag, which makes it possible to identify at most 256 chips. In addition, as 20 kinds of the gene specific sequences (for example, gene specific sequences of ATP5B, GAPDH, GUSB, HMBS, HPRT1, RPL4, RPLP1, RPS18, RPL13A, RPS20, ALDOA, B2M, EEF1G, SDHA, TBP, VIM, RPLP0, RPLP2, RPLP27, and OAZ1), 20±5 bases in a part of 109±8 bases upstream from the poly-A tail of the target gene are used. This is for making the sizes of the PCR products uniform to be about 200 bases in the subsequent PCR amplification step. The uniformed PCR product sizes lead to an effect of eliminating a cumbersome step of size fraction purification (electrophoresis→cut out of gel→extraction/ purification of PCR products), making it possible to directly use the PCR products for the parallel amplification (emulsion PCR, etc.) from one molecule.

After the completion of synthesis of the $2^{nd}$ cDNA strands 304, a large amount of a buffer solution is allowed to flow from the upper common inlet 107 toward the upper common outlet 108 to flush out the mineral oil remaining in the areas 116 of the common supply flow channel 105. Since the purpose of allowing the buffer solution to flow is to connect again the flow channels between the four reaction chambers 102, a small amount of the mineral oil may remain in the areas 116.

(Steps 5 and 6)

Finally, PCR amplification by the common primer is implemented. First, 49 μL of sterilized water, 10 μL of 10×High Fidelity PCR Buffer (Invitrogen), 10 μL of 2.5 mM dNTP mix, 4 μL of 50 mM MgSO₄, 10 μL of 10 μM common sequence primer for PCR amplification (Forward), 10 μL of 10 μM common sequence primer for PCR amplification (Reverse), and 1.5 μL of Platinum Taq Polymerase High Fidelity (Invitrogen) are blended to produce a reagent. In addition, the solution filling the common suction flow channel 109 of the flow cell device 101 is discharged from the lower common outlet 110.

After that, the reagent produced is introduced into the common supply flow channel 105 through the upper common inlet 107 in the same manner as in the previous step. Subsequently, the entire flow cell device 101 is kept at 94° C. for 30 seconds, then the following cycle of three steps: at 94° C. for 30 seconds→at 55° C. for 30 seconds→at 68° C. for 30 seconds, are repeated 40 times. Finally, the entire flow cell device 101 is kept at 68° C. for 3 minutes, and then cooled to 4° C., thereby performing a PCR amplification step. This reaction is a common reaction. Accordingly, all the chips are subjected to PCR amplification under a common reagent condition so that the amplification efficiency is made uniform among the chips.

In the course of the amplification, desired parts of the 20 kinds of target genes are amplified. However, any PCR products have almost uniform sizes of 200±8 bases. Finally, the solution of the PCR amplification products accumulated in the solution is recovered. For the purpose of eliminating remaining reagents, such as free common sequence primers for PCR amplification (Forward/Reverse) and enzymes, contained in the solution, the solution is purified using the PCR Purification Kit (QIAGEN).

The obtained PCR products 215, which are sequences that can be analyzed for the sequence (strictly speaking, sequences for which a pretreatment of the sequence analysis (emulsion PCR, etc.) can be performed), are referred to as a sequencing library. In addition, even if amplification bias occurs among genes or molecules in this step, since the amplification bias can be corrected using molecule recognition tags after acquiring next generation sequencing data, a highly precise quantification data can be obtained.

By subjecting the sequencing library to a sequence analysis, gene expression levels can be obtained for each cell identification sequence and each chip identification sequence. That is, a number of cells equal to or lower than the number obtained as the product of the number of kinds of the cell identification sequences and the number of kinds of the chip identification sequences simultaneously introduced in the flow cell device can be analyzed at the same time. By this, it is possible to analyze a considerably larger number of the cells than the number of cell identification sequences previously introduced in the two-dimensional array chip.

In the above, an example where tens of kinds of gene specific sequence primers in which a common sequence for PCR amplification is added are used for cDNAs ($1^{st}$ cDNAs) produced on a bead surface to synthesize the $2^{nd}$ cDNA strands 304, which are then subjected to PCR amplification, is explained. Of course, the amplification technique is not limited to the PCR amplification, and another amplification method, such as rolling circle amplification (RCA), NASBA, a LAMP method, and the like may be used.

(Structure and Production Method of Two-Dimensional Array Chip)

Here, the structure and production method of the two-dimensional array chip 115 configured using the magnetic beads 601 will be explained with reference to FIG. 5. The two-dimensional array chip 115 is produced as the chip 503 made of PDMS (polydimethylsiloxane). In the chip 503, the cell capturing units 103, the nucleic acid capturing units 104 filled with the magnetic beads 601, and the flow channels 504 each connecting the cell capturing unit 103 and the nucleic acid capturing unit 104 are formed. Incidentally, the chip 503 is configured by a large number of recessed structures corresponding to nucleic acid capturing unit 104 and the flow channels 504 having a small diameter formed on the bottom surface (upper surface in the figure). This structure is produced by injection molding. The flow channels 504 are through holes having a diameter of 10 μm, and arranged in an array format intervals of 125 μm. The area of the upper surface side of the flow channel 504 corresponds to the cell capturing unit 103, and the area of the lower surface side of the flow channel 504 (recessed portion) corresponds to the nucleic acid capturing unit 104.

The chip 503 is a square with each side of 1.125 mm, and in the case of FIG. 5, $7^2$ of the cell capturing units 103 are disposed inside the chip 503. The number is an example, and may be $10^2$. A cylindrical through hole forming the recessed portion just under the cell capturing unit 103 has a diameter of 75 μm, and this space is filled with the magnetic beads 601 to form the nucleic acid capturing unit 104. On the under surface of the chip 503 in which the through holes are arranged in an array form, the pore array sheet 502 in which a large number of pores are arranged so as to correspond to the positions of the through holes (recessed portions) is disposed. The diameter of the pores in the pore array sheet 502 is 200 nm, which is smaller than the diameter 1 μm of the magnetic bead 601. By closing the opening of the lower surface side of the through holes (recessed portions) with the pore array sheet 502, the magnetic beads 601 remain to be held in the through hole (recessed portion). In addition, by the pores formed in the pore array sheet 502, solution flow between the upper surface side and the lower surface side (common suction flow channel 109) of the reaction chambers 102 is ensured.

The filling with the magnetic beads 601 is achieved by using an inkjet printer head. That is, with the chip 503 reversed vertically, each space as the nucleic acid capturing unit 104 is filled with 2 nL of a solution of the magnetic beads 601 to which the first DNA probes 201 having a different sequence attached for each individual area are immobilized. In the solution of the magnetic beads 601 to be used for this filling, the magnetic beads 601 having a diameter of 1 μm are suspended at a number density of $5 \times 10^9$/mL. The magnetic beads 601 have streptavidin immobilized thereon, and the first DNA probe 201 modified with a biotin group on the 5' end is immobilized via the streptavidin. When the solution of the magnetic beads 601 is ejected into the nucleic acid capturing units 104 using an inkjet printer head, since the inner walls of the pores in the pore array sheet 502 are hydrophilic surface, only the solvent water in the bead solution is absorbed by capillary action, and the magnetic beads 601 remains in the nucleic acid capturing unit 104.

As the pore array sheet 502, various materials, such as a monolith sheet made of a porous glass, a capillary plate obtained by slicing a bundle of capillaries, a nylon membrane, and a gel thin film may be used, and in the Example, a pore array sheet obtained by subjecting an alumina to anodic oxidization is used. Such a kind of the pore array sheet 502 may be produced by anodic oxidation, but is also commercially available as a product having a pore size of 20 nm to 200 nm, and a diameter of 25 mm. In the Example, as described above, a pore array sheet 502 having a pore size of 200 nm is used. The pores in the pore array sheet 502 act as the lower flow channels 501 connecting the nucleic acid capturing units 104 and the lower common flow channel 109.

Although the chip 503 in the above explanation is made of PDMS, a base plate made of a resin (polycarbonate, cyclic polyolefin, polypropylene) produced by nanoimprint technology or injection molding, or a commercially available nylon mesh or track-etched membrane may be used as the chip 503. Thermobonding may be used for bonding the chip 503 with the pore array sheet 502. The chip 503 and the pore array sheet 502 are integrated, thereby forming the two-dimensional array chip 115.

Incidentally, for immobilizing the first DNA probes 201 having a unique tag sequence on the magnetic beads 601, a different reaction tube is provided for each unique tag sequence, and in the tube, the magnetic beads 601 and the DNA probe solution are blended in a Tris buffer (pH 7.4) containing 1.5M NaCl and the mixture is rotated for 10 minutes to effect the bonding reaction.

The pore array sheet 502 produced in the above procedure can be repeatedly used, and for a gene group whose expression levels are to be known, the procedure in which a gene specific sequence primer-mix solution having a common sequence primer for PCR amplification (Reverse) added thereto is produced, synthesis of $2^{nd}$ cDNA strands, PCR amplification, and emPCR are conducted in the same manner as the above, and the products are analyzed by a next generation sequencer may be conducted. That is, by repeatedly using the cDNA library, it is possible to perform a highly precise expression distribution measurement for required kinds of genes.

(Single Cell Analysis Process: Second Regulation Method)

Subsequently, a process according to the above second regulation method will be explained. The second regulation method can also be implemented using the flow cell device 101 described above (FIG. 5, FIG. 6), and a sequencing library for next generation sequencer can be easily prepared.

Hereinunder, only differences from the first preparation method described before will be described. A difference in the step 1 is only a point that as a sequence of the first DNA probe 301 to be immobilized to the inner wall of the nucleic acid capturing unit 104 (FIG. 3), the common connection sequence 302 having a shorter base length of 10 bases is used instead of the common PCR primer (Reverse). The step 2 is exactly the same as in the first regulation method described above.

The difference in the step 3 is that the second DNA probe 303 used in the synthesis of the $2^{nd}$ cDNA strand does not contain a chip identification sequence. That is, the mixed solution of 20 kinds of the second DNA probes 303 is not introduced through the individual inlets 111, 112, 113, and 114 for each two-dimensional array chip 115, but the mixed solution of the second DNA probes 303 having the same sequences is introduced into all the two-dimensional array chips 115 from the upper common inlet 107 through the common supply flow channel 105, in the same manner as in the steps 1 and 2 in the first regulation method.

Furthermore, in the step 4, like in the first regulation method, the temperature of the entire flow cell device 101 is elevated to 72° C. for 6 minutes to effect a complementary strand extension reaction and synthesize a $2^{nd}$ cDNA strand. In the step 5, to the synthesized $2^{nd}$ cDNA strand 304, the third DNA probe 305 (composed of the PCR common 306, the second chip identification sequence 307, and the complementary sequence 308) is hybridized.

For implementing this process, 69 μL of sterilized water, 10 μL of 10×Ex Taq Buffer (TaKaRa Bio), 100 μL of 2.5 mM dNTP Mix, 10 μL of a mixed solution of the third DNA probes 308 including 10 kinds of chip identification tags having 10 μM of a common sequence for PCR amplification (Reverse) added thereto, and 1 μL of Ex Taq Hot start version (TaKaRa Bio) are blended, and the mixed reagent is introduced from the upper inlet 107 through the common supply flow channel 105 into the nucleic acid capturing units 104 of each reaction chamber 102 in the same manner as in the previous step. The 10 kinds of third DNA probes are individually introduced for the respective two-dimensional array chips. The introduction method is exactly the same as the first regulation method described above. Next, the temperature of the entire flow cell device 101 is elevated to 72° C. for 6 minutes to effect complementary strand extension reactions and complete introduction of the tag sequence. In the final step 6, PCR amplification is implemented in the same manner as in the first regulation method to build a sequencing library as the PCR amplification products 309.

[Single Cell Analysis Apparatus]

Figure 8:
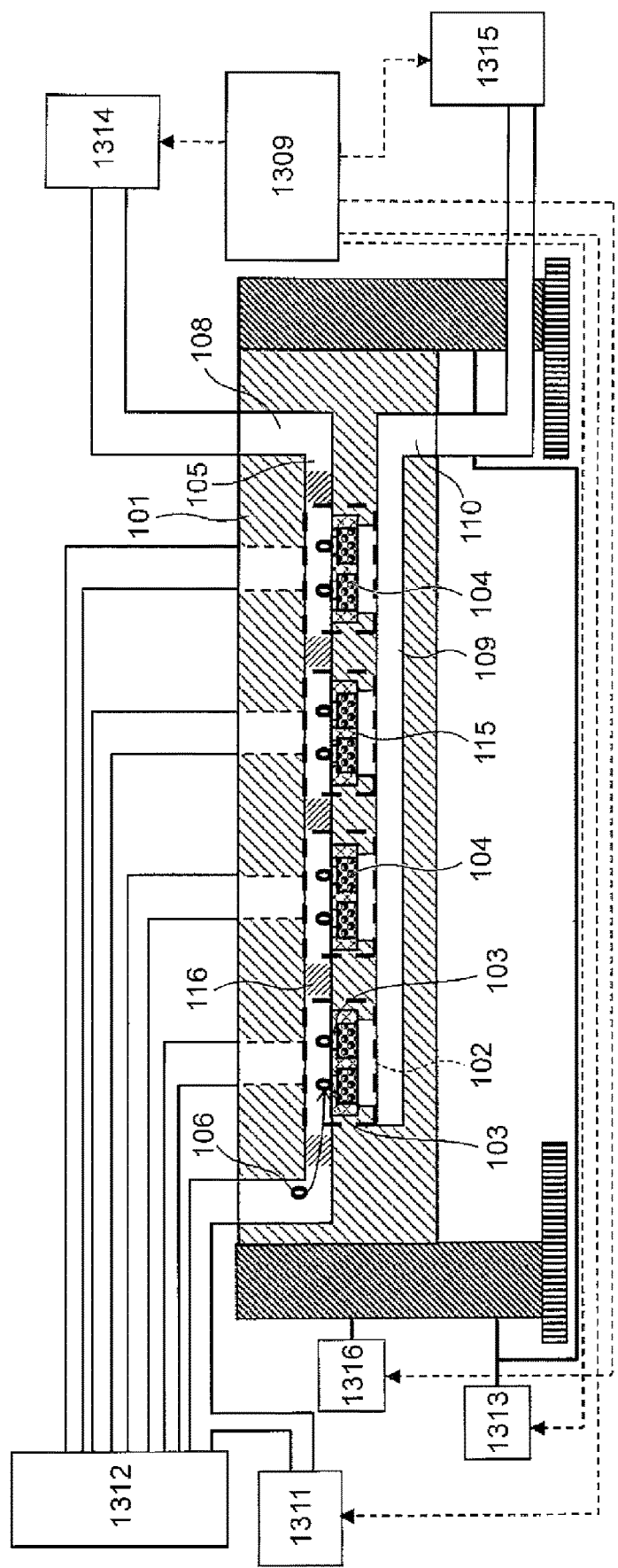
FIG. 8 shows a diagram of a configuration example of a single cell analysis apparatus.

FIG. 8 shows a configuration example of a single cell analysis apparatus that can automatically implement the first regulation method or the second regulation method using the flow cell device 101 described above. The single cell analysis apparatus implements the first regulation method or the second regulation method in an automatically controlled manner, and can introduce reagents into the flow cell device 101 to effect reactions.

FIG. 8 shows a configuration of the single cell analysis apparatus particularly with a focus on the controlling system of liquid feeding. A control computer 1309 in the single cell analysis apparatus appropriately controls a cell introduction controller 1311, a reagent introduction controller 1312, a stage controlling system 1313, an upper reagent discharger 1314, a lower reagent discharger 1315, and a temperature controlling system 1316.

The cell introduction controller 1311 controls introduction of the cells 106 into the flow cell device 101 for cells. The reagent introduction controller 1312 controls introduction of a cell lysate for crushing the cells 106, introduction of an enzyme reagent for cDNA synthesis or PCR amplification, introduction of the second and the third DNA probes, and introduction of a mineral oil or the like for separating the reaction chambers 102. The cell introduction controller 1311 and the reagent introduction controller 1312 are connected to the upper common inlet 107 via a common pipe. The stage controlling system 1313 controls variation of the observation field of the flow cell device 101 (an XYZ position of a stage on which the flow cell device 101 is placed) for microscopic observation. The upper reagent discharger 1314 controls discharge of unnecessary reagents, cells, a mineral oil for separating the reaction chambers 102, and the like. The upper reagent discharger 1314 and the upper common outlet are connected via a dedicated pipe. The lower reagent discharger 1315 controls: (1) introduction of the cells 106 into the two-dimensional array chips 115; (2) suction for introducing various enzyme reagents, the second and the third DNA probes, substrates, etc.; (3) discharge of nucleic acid amplification products prepared; and the like. The lower reagent discharger 1315 and the lower common outlet 110 are connected via a dedicated pipe. The temperature controlling system 1316 controls the temperature (reaction temperature) inside the flow cell device 101.

The cell introduction controller 1311 and the reagent introduction controller 1312 introduce the cells 106 and various reagents (enzyme reagents, substrates, the second and the third DNA probes, primers) which are stored at an appropriated temperature, at an appropriate timing, into the common supply flow channel 105 or the individual inlets 111, 112, 113, and 114 in the flow cell device 101. For this reason, the cell introduction controller 1311 and the reagent introduction controller 1312 appropriately open and close a switching valve to switch pipes inside the apparatus.

The upper reagent discharger 1314 and the lower reagent discharger 1315 include a syringe pump or the like therein and suck and discharge reagents or a cell solution. Of course, these dischargers are configured so that waste liquid accumulated in the syringe can be discharged into a waste liquid bottle or the like. The temperature controlling system 1316 has a capability of controlling the temperature of the reaction chambers 102 to a temperature between 4° C. to 98° C., and is composed of a Peltier element and a controller thereof. The stage controlling system 1313 will be explained in Example 3.

When the first regulation method is automatically implemented, the single cell analysis apparatus shown in FIG. 8 implements a series of controls described below using the control computer 1309.

(Step 1)

In this step, the control computer 1309 implements a capturing process of the cells 106 and a capturing process of the nucleic acids 206. First, the control computer 1309 controls the cell introduction controller 1311 to introduce a solution containing the cells 106 from a solution tube to the upper common inlet 107. Next, the control computer 1309 controls the upper reagent discharger 1314 to once fill the reaction chambers 102 with the cell solution. Subsequently, the control computer 1309 controls the lower reagent discharger 1315 to capture the cells 106 on the two-dimensional array chips 115.

Next, the control computer 1309 controls the upper reagent discharger 1314 to suck excess cells 106 in the cell solution, and at the same time, introduce a cell lysate from the upper common inlet 107. In the same manner as for introduction of the cells 106, the control computer 1309 controls the lower reagent discharger 1315 to suck the cell lysate through the common suction flow channel 109 and capture the nucleic acids (mRNA) 206 into the nucleic acid capturing units 104. In this time, the control computer 1309 controls the temperature in the reaction chambers 102 to approximately 25° C. (a temperature at which capture of mRNAs occur highly efficiently) using the temperature controlling system 1316.

(Step 2)

For synthesizing $1^{st}$ cDNA strands, the control computer 1309 uses the reagent introduction controller 1312 to introduce a cDNA synthesis reagent from the upper common inlet 107. Next, the control computer 1309 uses the upper reagent discharger 1314 to fill the reaction chambers 102 with the reagent, and then uses the lower reagent discharger 1315 to apply a negative pressure to the lower common outlet 110. By this, the cDNA synthesis reagent is introduced from the reaction chambers 102 into the two-dimensional array chips 115.

The control computer 1309 uses the temperature controlling system 1316 to appropriately control the temperature of the flow cell device 101 for a certain period of the reaction time, completing the cDNA synthesis reaction. After that, the control computer 1309 uses the temperature controlling system 1316 to heat the reaction chambers 102 to 85° C. to thereby deactivate the cDNA synthesis enzyme, and introduce an RNase reagent into the two-dimensional array chips 115 in the same manner as the above.

(Steps 3 and 4)

The control computer 1309 controls the reagent introduction controller 1312 to introduce an enzyme reagent solution into the upper common inlet 107. The reagent introduction controller 1312 and the upper common inlet 107 are connected via a pipe. By this, in the same manner as in the above, the reagent is introduced into the two-dimensional array chips 115 in the reaction chambers 102 connected to the common supply flow channel 105. Next, the control computer 1309 introduces a buffer containing a mineral oil and a salt from the upper common inlet 107, and simultaneously sucks the buffer from the upper reagent discharger 1314. By this, the four reaction chambers 102 serially connected with the common supply flow channel 105 are separated from each other by the mineral oil. After that, the control computer 1309 connects buffer solutions containing the second DNA probes 208 having different chip identification sequences to the respective individual inlets 111, 112, 113, and 114 through control of the reagent introduction controller 1312, and further controls the lower reagent discharger 1315 to introduce the DNA probe solutions into the two-dimensional array chips 115.

(Steps 5 and 6)

When synthesis of the $2^{nd}$ cDNA strands 304 is completed, the control computer 1309 controls the reagent introduction controller 1312 to introduce a washing buffer into the upper common inlet 107, and simultaneously controls the upper reagent discharger 1314 to discharge the mineral oil used for separation of the reaction chambers 102 from the areas 116 in the common supply flow channel 105. After that, the control computer 1309 introduces common primers and a PCR amplification reagent into the upper common inlet 107, and in the same manner as in the above step, introduces the reagent into the two-dimensional array chips 115. After that, the control computer 1309 uses the temperature controlling system 1316 to apply prescribed temperature cycles for a PCR reaction to perform PCR amplification.

Incidentally, when the aforementioned second regulation method is implemented, the control computer 1309 introduces the second DNA probes 208 from the upper common inlet 107, and introduces the third DNA probes 308 from the individual inlets 111, 112, 113, and 114. The other operations are performed basically in the same manner as in the first regulation method.

Example 2

In the Example, another technique is explained for building a cDNA library, while maintaining the information of: which cell, among the cell group arranged in an array form, the nucleic acids (mRNAs) 206 contained in each cell 106 is derived from. In the Example, as the nucleic acid capturing units 104, instead of the magnetic beads 601, a pore array sheet in which DNA probes are immobilized is used. By using the pore array sheet, when the two-dimensional array chips 115 are set on the flow cell device 101, a risk of the magnetic beads 601 being mixed among the nucleic acid capturing units 104 can be avoided.

Figure 9:
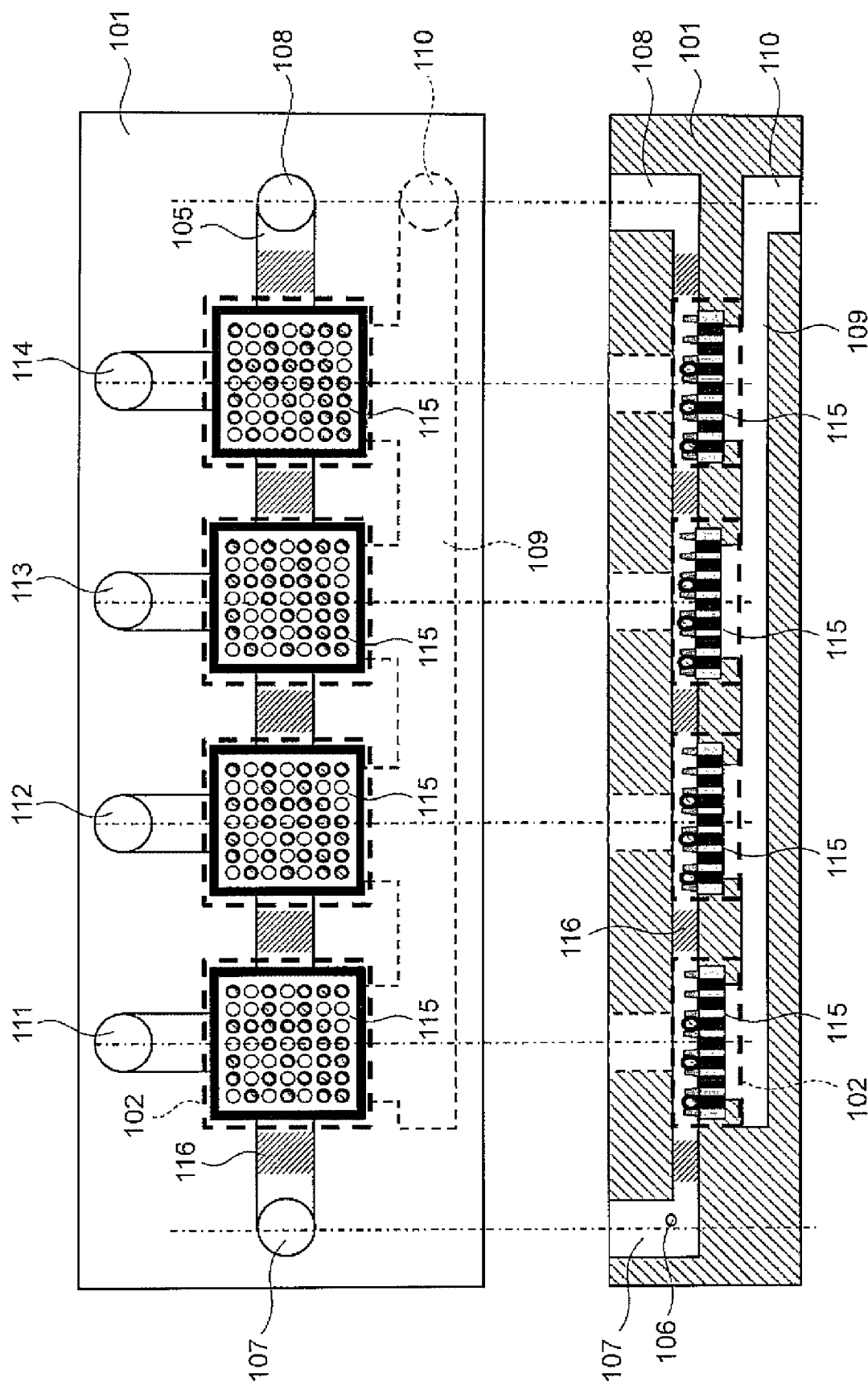
FIG. 9 shows diagrams of a configuration of a flow cell device according to Example 2.
Figure 10:
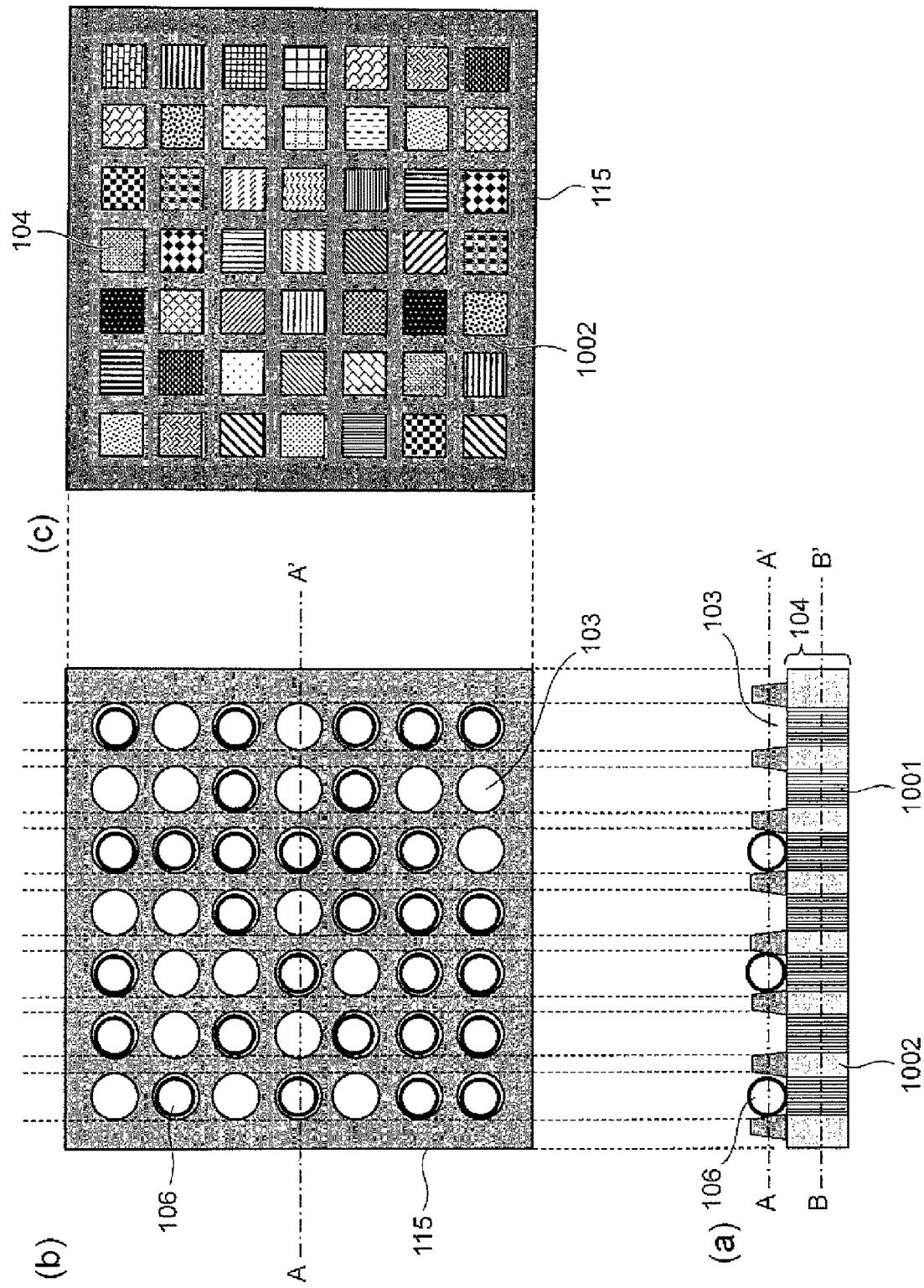
FIG. 10 shows diagrams of a configuration of a two-dimensional array chip used in Example 2.
Figure 11:
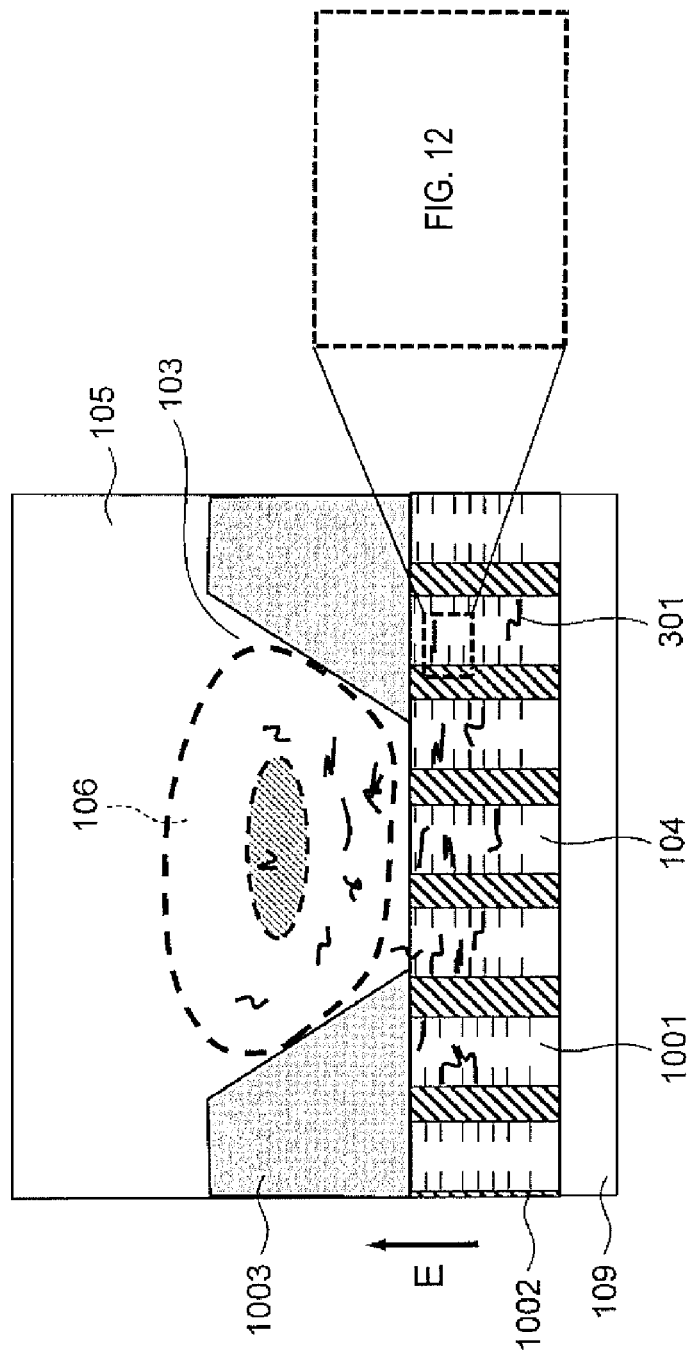
FIG. 11 shows an enlarged view of a unit structure of the two-dimensional array chip used in Example 2.
Figure 12:
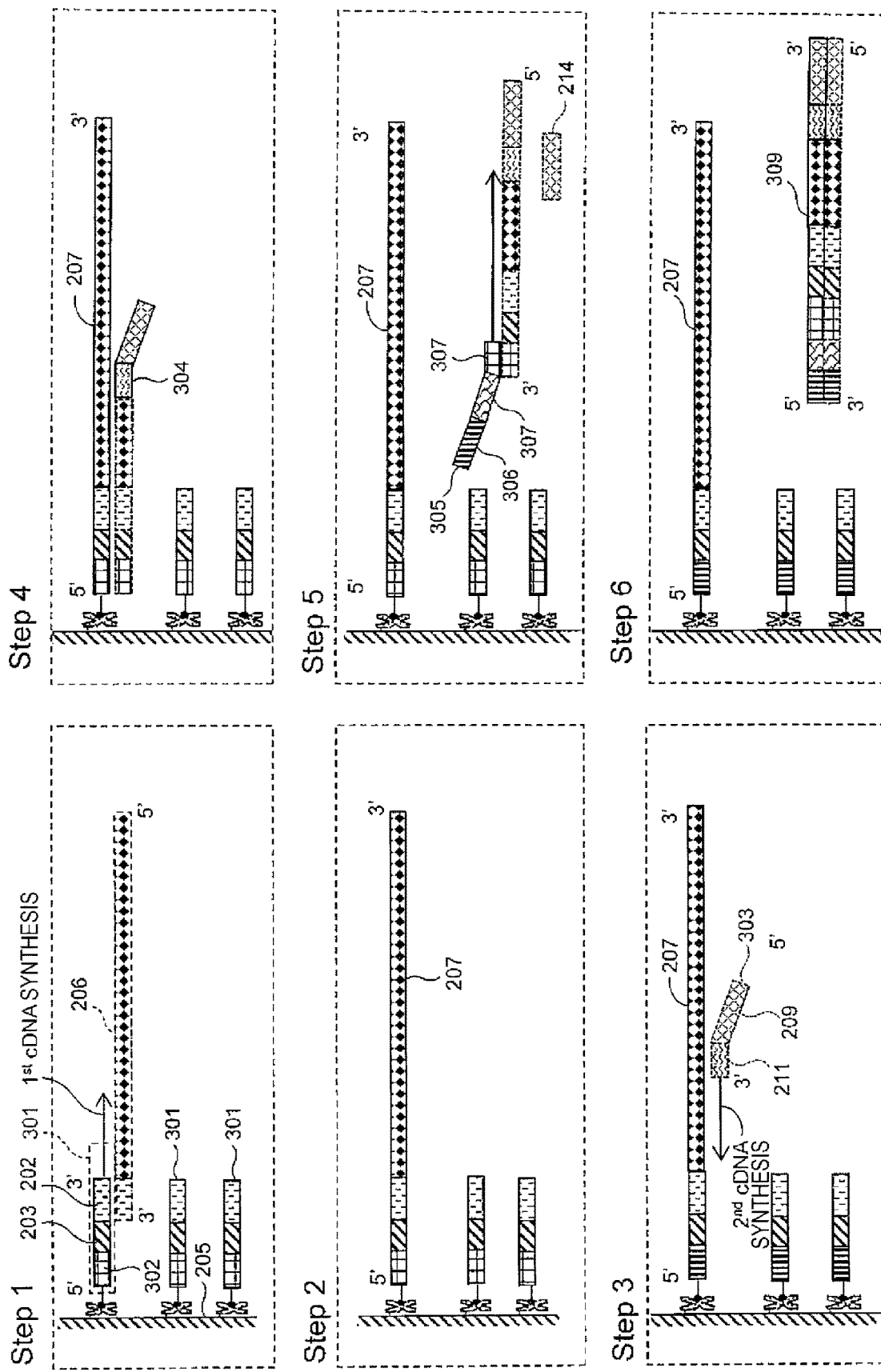
FIG. 12 shows diagrams of a reaction course implemented in Example 2.

FIG. 9 shows a structure of the flow cell device 101 according to the Example, and FIG. 10 shows a structure of the two-dimensional array chip 115 used in the Example. FIG. 11 shows an enlarged cross section of the two-dimensional array chip 115, and FIG. 12 shows a reaction course for the second regulation method.

Hereinunder, only differences from Example 1 will be explained. The structure of the flow cell device 101 is different only in a point that the two-dimensional array chip 115 is produced by a semiconductor process. The concrete structure of the two-dimensional array chip 115 is as shown in FIG. 10. FIG. 10($a$) is a cross section perpendicular to the surface of the two-dimensional array chip 115. FIG. 10($b$) is an A-A' cross-section of FIG. 10($a$) viewed from the upper surface side, and FIG. 10($c$) is a B-B' cross-section of FIG. 10($a$) viewed from the upper surface side.

In the case of the Example, as the pore array sheet configuring the nucleic acid capturing units 104, through holes 1001 having a diameter of 0.3 μm are formed at pitches of 0.5 μm in an $SiO_2$ film 1002 having a thickness of 5 μm. In addition, in the Example, the first DNA probes 301 are immobilized on the inner wall surfaces of the through holes 1001 which function as the nucleic acid capturing unit 104 by using a silane coupling agent. Incidentally, the diameter (the uppermost portion) of a tapered recessed portion configuring the cell capturing unit 103 is 10 μm. The cell capturing units 103 are produced by forming openings in a polyimide resin film 1003 having a thickness of 10 μm using lithography.

Next, a method for immobilizing the first DNA probes 301 onto the nucleic acid capturing unit 104 will be explained. For subjecting the inner wall surfaces of through holes 1001 as the nucleic acid capturing units 104 to a silane treatment, an aqueous solution containing 0.3 mg/ml of a silane coupling agent GTMSi (GTMSi: 3-glycidoxypropyltrimethoxysilane, Shin-Etsu Chemical, Co., Ltd.) and 0.02% acetic acid as an acid catalyst is introduced in a reaction device to effect a reaction for 2 hours. The inside of the reaction device is washed by introducing ethanol in an amount 100 times the inner volume of the device into the reaction device, all the solution is discharged, and further, a thermal reaction is effected at 110° C. for 2 hours.

Next, a 1 μM streptavidin solution is introduced into a reaction device, and allowed to react at a room temperature for 6 hours to immobilize streptavidin in areas of the reaction device. Subsequently, unreacted glycide groups are blocked, and for removing excess DNA probes, a borate buffer (pH 8.5) containing 10 mM of glycine, 0.01% SDS, and 0.15 M NaCl are introduced in an amount of 10 times the inner volume of the device over 5 minutes while being discharged, and furthermore, 30 mM sodium citrate buffer (2×SSC, pH 7.0) containing 0.01% SDS and 0.3 M NaCl heated to 60° C. are introduced in an amount of 10 times the inner volume while being discharged. Finally, 10 mM Tris containing 0.1% Tween 20 is introduced in an amount of 100 times the inner volume while being discharged, completing the washing.

Furthermore, a 10 mM Tris HCl solution containing 10 µM of the first DNA probes 301 whose 5' end is modified with biotin, 1 M of NaCl, and 0.1% of Tween 20 are introduced in an amount equal to the inner volume into the reaction device to effect a reaction for 30 minutes, and then the 2×SSC buffer heated to 60° C. in an amount of 10 times is introduced and discharged again. After that, a Tris HCl buffer containing 0.1% Tween 20 in an amount of 100 times is introduced into the reaction device while being discharged to wash the device, completing the immobilization reaction.

Incidentally, the reaction process is the same as in the second regulation method of Example 1.

Example 3

In Examples 1 and 2 described above, the flow cell device 101 in which the common supply flow channel 105 (the upper common inlet 107 and the upper common outlet 108 correspond thereto) and individual fluid channels (the individual inlets 111, 112, 113, and 114 correspond thereto) are formed on the upper surface side, and the common suction flow channel 109 (the lower common outlet 110 corresponds thereto) is formed on the lower surface side is used.

Figure 13:
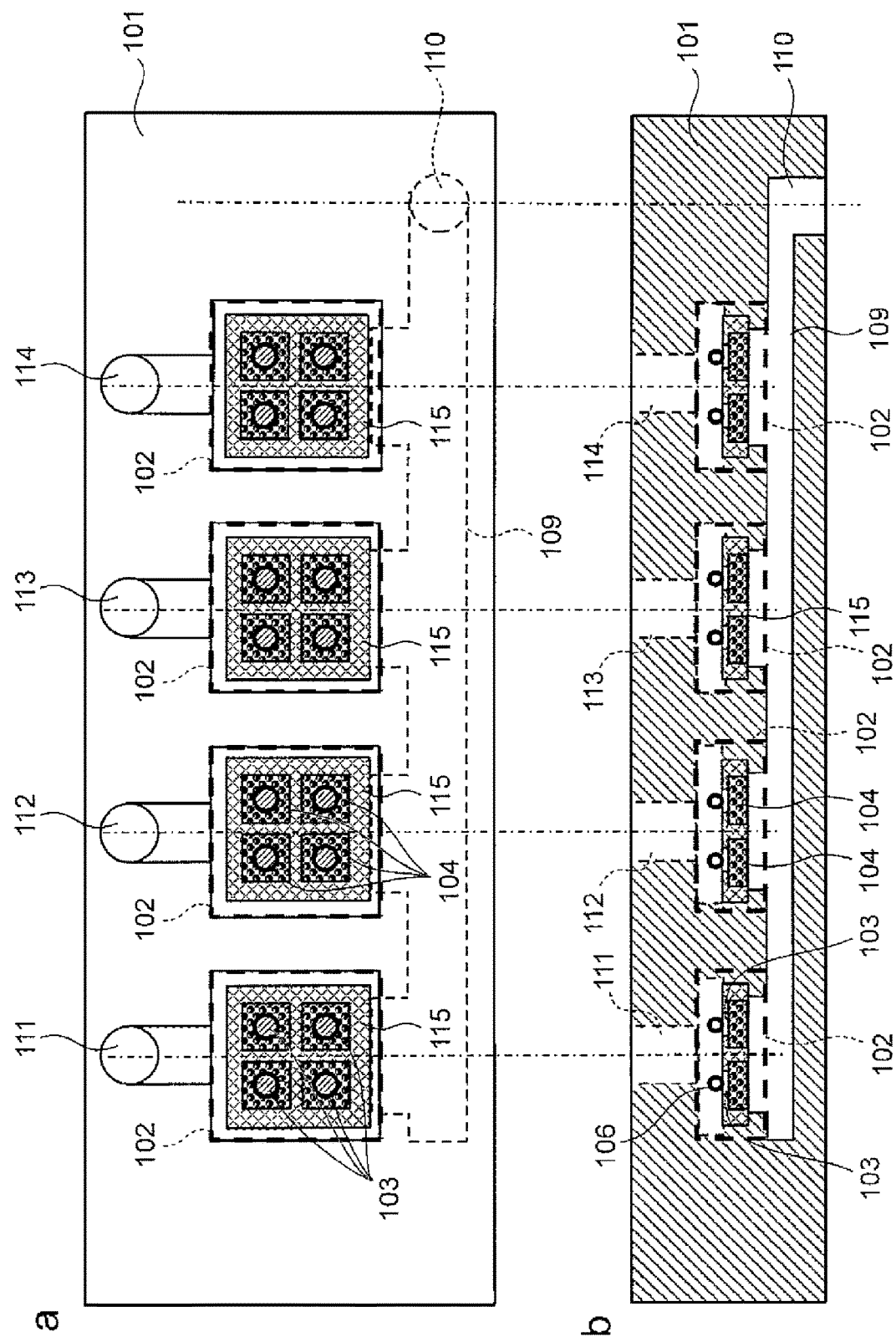
FIG. 13 shows diagrams of a configuration of a flow cell device according to Example 3.
Figure 14:
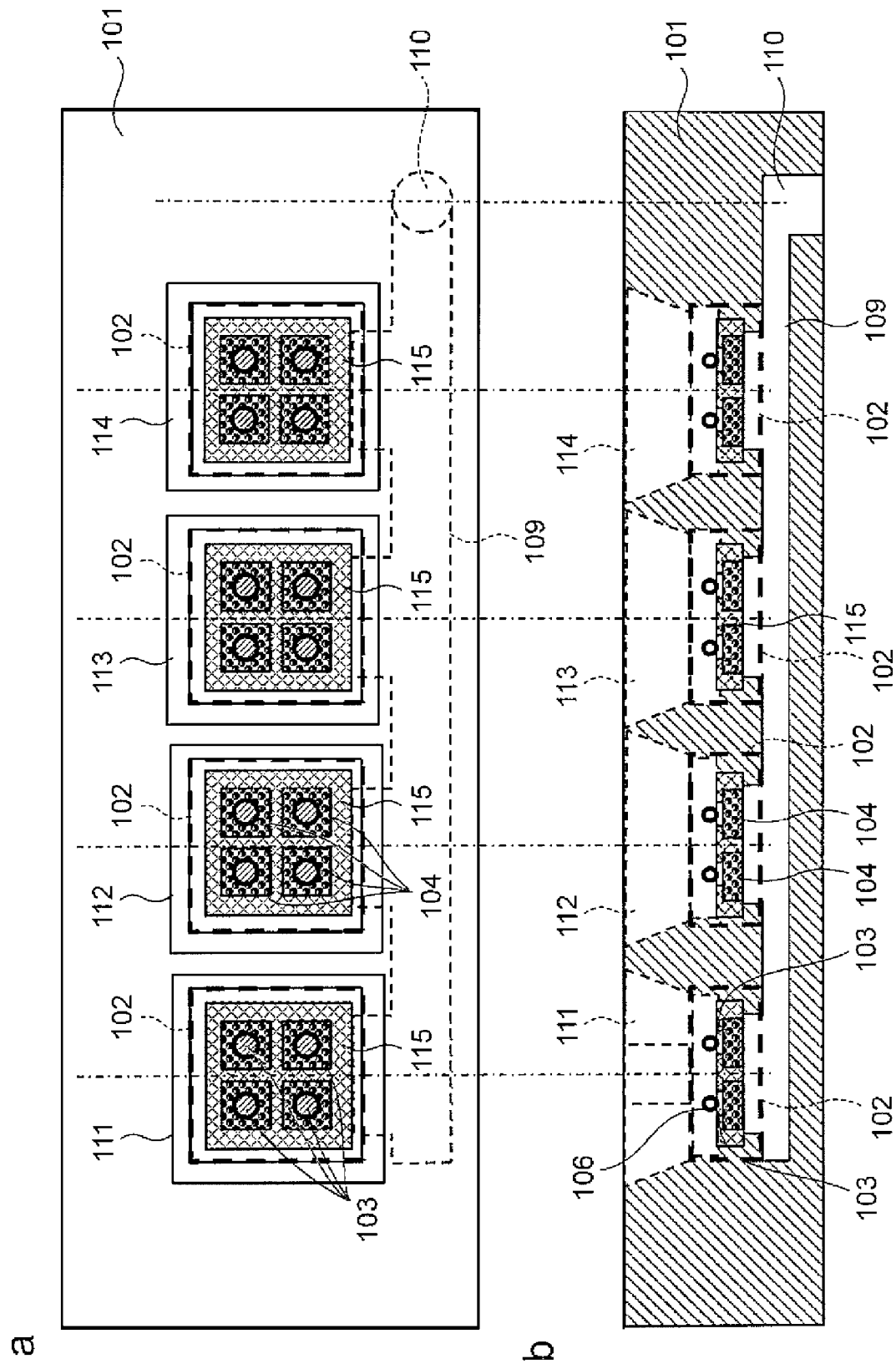
FIG. 14 shows diagrams of another configuration of the flow cell device according to Example 3.

In the Example, as shown in FIG. 13 and FIG. 14, the flow cell device 101 having a structure obtained by removing the upper common inlet 107, the common supply flow channel 105, and the upper common outlet 108 from the upper surface side of the flow cell device 101 (FIG. 1) is used. In particular, the flow cell device 101 shown in FIG. 14 has openings in the upper portion of the two-dimensional array chips 115 so that a cell solution can be directly added dropwise onto the upper surface of the two-dimensional array chips 115 and the upper surface can be directly observed with a microscope. Other configurations are the same as in the case of FIG. 1. The flow cell device 101 according to the Example has a simpler structure than the flow cell device 101 of Examples 1 and 2.

Figure 15:
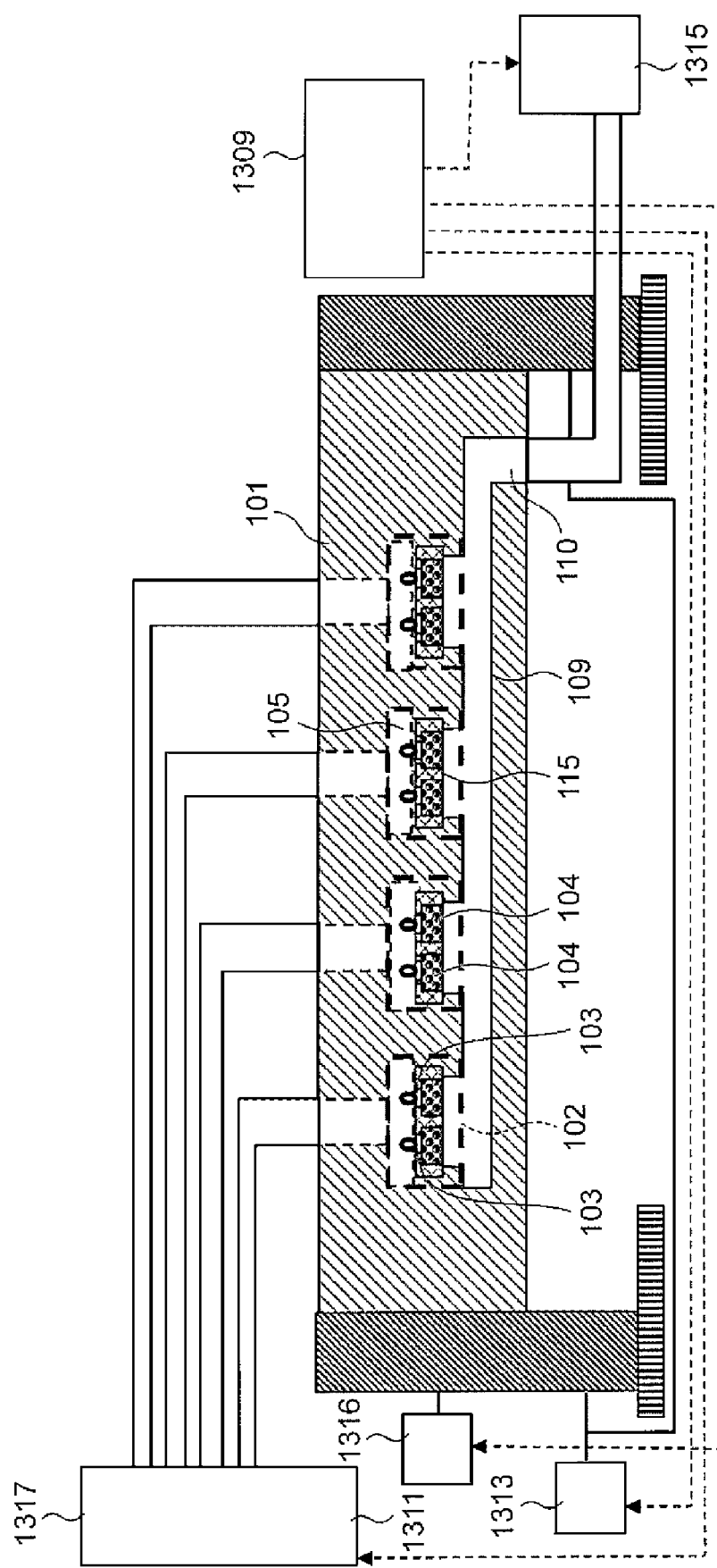
FIG. 15 shows a diagram of a configuration example of a single cell analysis apparatus used in Example 3.

FIG. 15 shows a configuration example of a single cell analysis apparatus used in the Example. This is different from the single cell analysis apparatus of Examples 1 and 2 shown in FIG. 8 in that, in the cell introduction controller according to the Example, instead of the reagent introduction controller 1312 for introducing enzyme reagents and DNA probes, a cell/reagent introduction controller 1317 that has both of the functions is provided and introductions of the cells 106 and reagents are realized through the four individual inlets 111 to 114. In the case of the Example, when an identical solution is introduced into the four reaction chambers 102, the identical solution is introduced to the four individual inlets 111 to 114, whereas when an individual solution is introduced into each of the reaction chambers 102, the respective solutions are introduced to the four individual inlets 111 to 114.

A reagent or the like that is introduced from the upper common inlet 107 in Examples 1 and 2 is, in the case of the Example, introduced through the individual inlets 111 to 114. Incidentally, the composition and the amount of the reagents or the like introduced in the Example are the same as in Examples 1 and 2. In addition, in Examples 1 and 2, the reaction chambers 102 are filled with a solution by the upper reagent discharger 1314, and then the reagent is introduced into the two-dimensional array chips 115 using the lower reagent discharger 1315. However, in the Example, a reagent in such an amount that the reaction chamber 102 in the upper portion of the two-dimensional array chip 115 is filled with the reagent or that the reagent just covers the upper surface of the two-dimensional array chip 115 is introduced from the individual inlets 111 to 114, and then the common suction flow channel 109 is controlled to be a negative pressure using the lower reagent discharger 1315, whereby the reagent can be introduced into the two-dimensional array chip 115.

In addition, in the case of the Example, since there is no need to separate the reaction chambers 102 from one another, the control program for implementing the steps of introduction of a mineral oil, etc. and washing is not required. The other operations of the device are basically the same as in Example 1.

Example 4

In a gene expression analysis using the two-dimensional array chips 115, a cell capturing position on a flat surface device such as the flow cell device 101 (including a pore array sheet) can be correlated to a result of the gene expression analysis. For example, before the cell 106 is crushed for the gene expression analysis and a detailed gene expression analysis is performed, acquisition of the shape of the cell 106 in the viable state, quantification of genes and proteins by fluorescence staining, or acquisition of a Raman imaging is implemented, and the data thereof can be correlated to the data of the gene expression analysis. In the Example, a system configuration for realizing this function will be explained.

Figure 16:
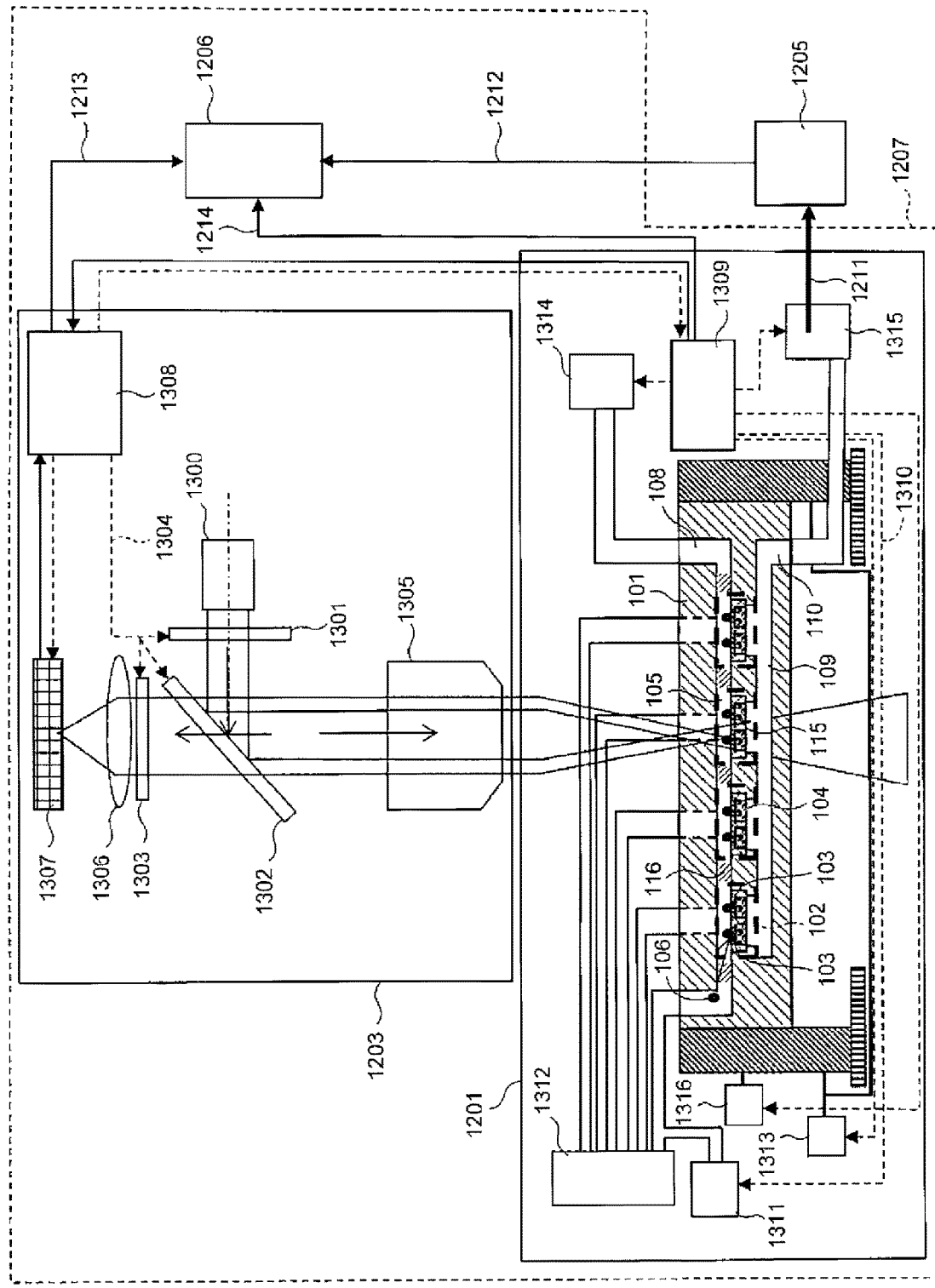
FIG. 16 shows a diagram of a configuration example of single cell analysis apparatus used in Example 4.

FIG. 16 shows a configuration in which the single cell analysis apparatus (FIG. 8) is combined with an optical microscope. FIG. 16 shows a state where the cells 106 are captured on the two-dimensional array chips 115 of the flow cell device 101. A flow system 1201 corresponds to the single cell analysis apparatus (FIG. 8), and like in the above examples, extraction of nucleic acids (mRNAs) 206 from the cells 106 and amplification thereof are implemented in the flow cell device 101. In a position above the flow system 1201, an optical microscope 1203 is disposed. An arrow 1211 shows movement of an amplification product. Based on a sequencing library as an amplification sample prepared with the flow cell device 101, a next generation (large scale) DNA sequencer 1205 determines sequences of the cell 106.

In the case of the Example, prior to the determination of the sequences, observation of the cell 106 whose position on the flow cell device 101 has been identified is implemented by the optical microscope 1203. The thin line arrow in the figure shows a direction of the information movement. Examples of the optical microscope 1203 include a phase contrast microscope, a differential interference microscope, a fluorescence microscope, a laser scanning confocal fluorescence microscope, a Raman microscope, a no-linear Raman microscope (CARS microscope, SRS microscope, RIKE microscope), and an IR microscope. The information obtained by the optical microscope 1203 is small in terms of gene information.

However, the optical microscope 1203 is capable of measuring the cell 106 basically in the viable state. That is, a time-dependent change of the cell 106, for example, of the response of the cell to a stimulation can be measured in real time. By utilizing a device in which the positional information on the flow cell device 101 is stored, detailed information of the gene expression can be correlated to the information including the time-dependent change from the optical microscope.

For realizing the correlation, in the Example, an information integration system 1206 is provided for integrating sequence information 1212 from the next generation (large scale) DNA sequencer 1205, information 1213 from the optical microscopic image 1203, and positional information 1214 to which a tag sequence is correlated. A minimum configuration of the information integration system 1206 for integrating the measurement information of the cell 106 is a system 1207 excluding the next generation (large scale) DNA sequencer 1205, and has functions to input information from and output a sample (nucleic acid amplification products) into, the next generation (large scale) DNA sequencer 1205.

Next, the flow system 1201 will be explained. FIG. 16 shows a state where the cells 106 are captured on a pore array sheet constituting the flow cell device 101. By causing a protein to be measured (for example, p53) to express GFP or by immunostaining the protein, a fluorescent substance has been introduced into the certain protein in the cell 106. The data of the expressed protein level for the individual cell 106 can be correlated to the gene expression level obtained by crushing the cell 106, then processing the cell into a sample on the pore array sheet, and performing quantification by DNA sequencing. In this case, for recognizing the cell 106, the nucleic acids are stained with DAPI to recognize the cell nuclei, and thus the position of the cell is identified by a fluorescence microscope.

For a protein, the time-dependent change can be traced since the protein is measured by expression of GFP, but the number of kinds of proteins that can be simultaneously measured is several kinds or so. On the other hand, 100 kinds or so can be analyzed at a time in a gene expression analysis by sequencing, and when probes are provided, analysis of 1000 kinds or so is also possible. Thus, detailed information on gene expression control in a cell can be obtained for each individual cell. A time-dependent change can however not be acquired in a gene expression analysis. Nevertheless, by combining both the analyses, if the data about what protein shows how gene expression are obtained in advance, it is possible to estimate information on the gene control based only on the protein expression data. The correlation of the fluorescence microscope data and the gene expression data and the estimation of information on the gene control are implemented by the information integration system 1206.

Next, a case where the optical microscope 1203 is a fluorescence microscope will be explained. The fluorescence microscope includes a light source 1300, an excitation filter 1301, a dichroic mirror 1302, and an emission filter 1303. As the light source 1300, for example, a mercury lamp is used. The excitation wavelength is determined by the excitation filter 1301. The light-receiving wavelength is selected by the emission filter 1303.

When plural kinds of fluorescent substances introduced into the cell 106 are simultaneously measured, a control computer 1308 selects the excitation filter 1301, the dichroic mirror 1302, and the emission filter 1303 by a control signal 1304 and measure only light from a certain fluorescent substance. A fluorescence image of the cell 106 is obtained by an objective lens 1305, an imaging lens 1306, and a CCD camera 1307. The control computer 1308 controls the components to obtain image data.

In addition, the control computer 1308 controls an XY stage 1310 to move the microscope image. In this time, the control computer 1308 can correlate a position coordinate on the pore array sheet, sequence data of a cell recognition tag, and a position coordinate on microscope image calculated from the position coordinate on the XY stage.

The nucleic acid amplification products obtained finally are subjected to a sequence analysis in the next generation (large scale) DNA sequencer 1205. In this time, emPCR and bridge amplification for the sequencing are implemented in this system. The positional information of the image and the cell recognition tag sequence information collated in the control computer 1308 are sent to the information integration system 1206, and the protein obtained from the fluorescence image is correlated to the gene expression levels. Furthermore, in the same system, a time-dependent change of the gene expression analysis data is estimated. By this, it is possible to measure the dynamics of the gene expression network.

In addition, the fluorescence microscope can be used not only for measurement inside a cell but also for measuring an amount of a substance, such as a captured cytokine cell, secreted from the cell by performing immunofluorescent stain with an antibody. Of course, the fluorescence microscope can be used for analyzing the gene expression level after crushing in the same manner. A combination of a differential interference microscope and a Raman microscope can also be used instead of the fluorescence microscope.

Other Examples

The present invention is not limited to the above examples and includes various modifications. For example, the above examples are illustrated in detail to assist understanding of the present invention, but not all the configurations described above are required to be provided. In addition, part of any example may be replaced with a configuration of any other example. Further, a configuration of any example may be added to a configuration of any other example. Further, part of a configuration of any example may be added to, eliminated from, or replaced with part of a configuration of any other example.

In addition, the configurations, functions, processing units, processing means, and the like described above may be partially or entirely realized by a hardware, for example, by designing them with an integrated circuit. Further, each of the configurations, functions, and the like described above may be realized by a processor understanding programs for realizing the functions and implementing the programs (that is, in a manner of software). Information for realizing each function, such as programs, tables, or files may be stored in a recording device, such as a memory, a hard disk, and an SSD (solid state drive), or a storing medium such as an IC card, an SD card, and a DVD. In addition, the control lines and information lines show those that are considered necessary for the explanation, and do not represent all the control lines and information lines required for the product. In practice, almost all the configurations are substantially connected to each other.

REFERENCE SIGNS LIST

101: Flow cell device
102: Reaction chamber
103: Cell capturing unit
104: Nucleic acid capturing unit
105: Common supply flow channel
106: Cell
107: Upper common inlet
108: Upper common outlet
109: Common suction flow channel
110: Lower common outlet
111, 112, 113, 114: Individual inlet
115: Two-dimensional array chip
116: Area 201: First DNA probe
202: Capturing sequence
203: Cell identification sequence
204: Common sequence
206: Nucleic acid (mRNA)
207: $1^{st}$ cDNA Strand
208: Second DNA probe
209: Common primer
210: Chip identification sequence
211: Gene specific probe
212: $2^{nd}$ cDNA
213, 214: Common primer
215: PCR product
301: First DNA probe
302: Common connection sequence
303: Second DNA probe
304: $2^{nd}$ cDNA Strand
305: Third DNA probe
306: PCR Common primer
307: Second chip identification sequence
308: Complementary sequence
309: PCR Amplification product
501: Lower flow channel
502: Pore array sheet
503: Chip
601: Magnetic bead
1001: Through hole
1002: $SiO_2$ Film
1201: Flow system
1203: Optical microscope
1205: Next generation (large scale) DNA sequencer
1206: Information integration system
1207: System excluding DNA sequencer 1205
1212: Sequence information
1213: Information
1214: Positional information
1300: Light source
1301: Excitation filter
1302: Dichroic mirror
1303: Emission filter
1304: Control signal
1305: Objective lens
1306: Imaging lens
1307: CCD Camera
1308: Control computer
1309: Control computer
1311: Cell introduction controller
1312: Reagent introduction controller
1313: Stage controlling system
1314: Upper reagent discharger
1315: Lower reagent discharger
1316: Temperature controlling system
1317: Cell/reagent introduction controller

The invention claimed is:

1. A flow cell device for single cell analysis, comprising:
a plurality of reaction chambers each including one or more cell capturing units each configured to capture a single cell and one or more nucleic acid capturing units connected in a one-on-one relationship to the one or more cell capturing units via respective flow channels;
a first liquid flow channel that is commonly connected to the plurality of reaction chambers on a first surface side;
a plurality of second liquid flow channels that are connected to the plural reaction chambers in a one-on-one relationship on the first surface side; and
a third liquid flow channel that is commonly connected to the plural reaction chambers on a second surface side opposite to the first surface,
wherein each of the nucleic acid capturing units has a porous structure or a structure in which a plurality of beads are packed,
wherein each of the nucleic acid capturing units has immobilized therein one or more mRNA-capturing probes each including a DNA sequence for identifying the respective nucleic acid capturing unit thereof, and
wherein each of the cell capturing units has an opening with a first diameter configured to capture a single cell, and each of the nucleic acid capturing units includes the porous structure or the structure in which the plurality of beads are packed and having a second diameter larger than the first diameter.

2. The flow cell device for single cell analysis according to claim 1, wherein the one or more mRNA-capturing probes each includes the DNA sequence for identifying the respective nucleic acid capturing unit thereof and a capturing sequence for capturing mRNA from the single cell captured by the respective cell capturing unit connected thereto.

3. The flow cell device for single cell analysis according to claim 1, wherein all inner walls of the plurality of reaction chambers have been subjected to a hydrophilic treatment and an inner wall surface of an area of the first liquid flow channel that connects the plurality of reaction chambers has been subjected to a hydrophobic treatment.

4. The flow cell device for single cell analysis according to claim 1, wherein each of the beads has a third diameter and each of the nucleic acid capturing units are connected by a plurality of lower flow channels to the third liquid flow channel, each of the lower flow channels having a fourth diameter smaller than the third diameter.

5. The flow cell device for single cell analysis according to claim 4, wherein the cell capturing units are disposed on the first surface side and the plurality of the lower flow channels are disposed in a pore array sheet on the second surface side.

6. A flow cell device for single cell analysis, comprising:
a plurality of reaction chambers each including one or more cell capturing units each configured to capture a single cell and one or more nucleic acid capturing units connected in a one-on-one relationship to the one or more cell capturing units via respective flow channels;
a plurality of first liquid flow channels that are connected to the plurality of reaction chambers in a one-on-one relationship on a first surface side; and
a second liquid flow channel that is commonly connected to the plurality of reaction chambers on a second surface side opposite to the first surface,
wherein each of the nucleic acid capturing units has a porous structure or a structure in which a plurality of beads are packed,
wherein each of the nucleic acid capturing units has immobilized therein one or more mRNA-capturing probes each including a DNA sequence for identifying the respective nucleic acid capturing unit thereof, and
wherein each of the cell capturing units has an opening with a first diameter configured to capture a single cell, and each of the nucleic acid capturing units includes the porous structure or the structure in which the plurality of beads are packed and having a second diameter larger than the first diameter.

7. The flow cell device for single cell analysis according to claim 6, wherein the one or more mRNA-capturing probes each includes the DNA sequence for identifying the respective nucleic acid capturing unit thereof and a capturing sequence for capturing mRNA from the single cell captured by the respective cell capturing unit connected thereto.

8. The flow cell device for single cell analysis according to claim 6, wherein the first liquid flow channel is formed as an opening of the reaction chamber for exposing the cell capturing unit to the outside.

9. The flow cell device for single cell analysis according to claim 6, wherein each of the beads has a third diameter and each of the nucleic acid capturing units are connected by a plurality of lower flow channels to the third liquid flow channel, each of the lower flow channels having a fourth diameter smaller than the third diameter.

10. The flow cell device for single cell analysis according to claim 9, wherein the cell capturing units are disposed on the first surface side and the plurality of the lower flow channels are disposed in a pore array sheet on the second surface side.

11. A single cell analysis apparatus, comprising:
a stage on which a flow cell device for single cell analysis is placed, the flow cell device including:
a plurality of reaction chambers each including one or more cell capturing units each configured to capture a single cell and one or more nucleic acid capturing units connected in a one-on-one relationship to the one or more cell capturing units via respective flow channels,
a plurality first liquid flow channels connected to the plurality of reaction chambers in a one-on-one relationship on a first surface side, and
a second liquid flow channel commonly connected to the plurality of reaction chambers on a second surface side opposite to the first surface;
a stage controlling system configured to control a position of the stage;
a first introduction controller configured to individually control introduction of a first liquid into the plurality of first fluid flow channels; and
a discharge controller configured to control discharge of a second liquid from the second fluid flow channel,
wherein each of the nucleic acid capturing units has a porous structure or a structure in which a plurality of beads are packed, and
wherein each of the nucleic acid capturing units has immobilized therein one or more mRNA-capturing probes each including a DNA sequence for identifying the respective nucleic acid capturing unit thereof, and wherein each of the cell capturing units has an opening with a first diameter configured to capture a single cell, and each of the nucleic acid capturing units includes the porous structure or the structure in which the plurality of beads are packed and having a second diameter larger than the first diameter.

12. The single cell analysis apparatus according to claim 11, further comprising:
a third liquid flow channel that is commonly connected to the plurality of reaction chamber on the first surface side of the flow cell device;
a second introduction controller configured to control introduction of a third liquid into the third liquid flow channel; and
a second discharge controller configured to control discharge of the third liquid from the third liquid flow channel.

13. The single cell analysis apparatus according to claim 11, further comprising:
an optical microscope for observing the flow cell device for single cell analysis, and correlating information acquired from an observation area to positional information acquired from the stage controlling system;
a DNA sequencer for analyzing a sequence of a nucleic acid amplification product obtained for each of the nucleic acid capturing units of the flow cell device for single cell analysis, and correlating the analysis result to the positional information acquired by the stage controlling system; and
an information integration system for integrating the information acquired from an observation area by the optical microscope and the analysis result for each of the nucleic acid capturing units acquired by the DNA sequencer.

14. The single cell analysis apparatus according to claim 11, wherein each of the beads has a third diameter and each of the nucleic acid capturing units are connected by a plurality of lower flow channels to the third liquid flow channel, each of the lower flow channels having a fourth diameter smaller than the third diameter.

15. The single cell analysis apparatus according to claim 14, wherein the cell capturing units are disposed on the first surface side and the plurality of the lower flow channels are disposed in a pore array sheet on the second surface side.

* * * * *